United States Patent [19]

Djuric et al.

[11] Patent Number: 5,532,383

[45] Date of Patent: Jul. 2, 1996

[54] LEUKOTRIENE B₄ ANTAGONISTS

[75] Inventors: Stevan W. Djuric, Glenview; Stephen H. Docter, Mount Prospect; Stella S. Yu, Morton Grove, all of Ill.

[73] Assignee: G. D. Searle & Co., Chicago, Ill.

[21] Appl. No.: 445,059

[22] Filed: May 19, 1995

Related U.S. Application Data

[62] Division of Ser. No. 205,909, Mar. 3, 1994, Pat. No. 5,439,937, which is a division of Ser. No. 995,859, Dec. 23, 1992, Pat. No. 5,310,951, which is a continuation-in-part of Ser. No. 545,430, Jun. 28, 1990, Pat. No. 5,124,350.

[51] Int. Cl.⁶ ............... C07D 405/06; C07D 403/10; C07D 401/10; C07D 257/04
[52] U.S. Cl. ............... 546/196; 546/210; 548/252; 548/253
[58] Field of Search ............... 546/210, 196; 548/252, 253

[56] References Cited

U.S. PATENT DOCUMENTS

| | | | |
|---|---|---|---|
| 3,882,148 | 5/1975 | Augstein et al. | 260/345.2 |
| 4,281,008 | 7/1981 | Chamberlain et al. | 424/269 |
| 4,546,194 | 10/1985 | Miyano et al. | 549/401 |
| 4,565,882 | 1/1986 | Miyano et al. | 549/402 |
| 4,778,903 | 10/1988 | Miyano et al. | 549/407 |
| 4,889,871 | 12/1989 | Djuric et al. | 514/456 |

FOREIGN PATENT DOCUMENTS

| | | |
|---|---|---|
| 0017332 | 2/1980 | European Pat. Off. . |
| 0028063A1 | 9/1980 | European Pat. Off. . |
| 0079637 | 1/1982 | European Pat. Off. . |
| 0129906 | 6/1984 | European Pat. Off. . |
| 0150447 | 12/1984 | European Pat. Off. . |
| 0336068A1 | 2/1989 | European Pat. Off. . |
| 60-42378 | of 0000 | Japan . |

OTHER PUBLICATIONS

Appleton, R. A. et al. Antagonists Of Slow Reacting Substance Of Anaphlaxis. Synthesis Of A Series Of Chromone–2–Carboxylic Acids, *Journal of Medicinal Chemistry*, 20, 371–379 (1977).

Searle, G. D. & Co. Benzopyran Antimetabolites, *Chem. Abstracts*, 103, 699, Abstract No. [160389g](1985).

Sheard, P. et al. Antagonists of SRS–A And Leukotrienes, *Chem, Abstracts*, 97, 44, Abstracts No. [16807g](1982).

*Primary Examiner*—Nicky Chan
*Attorney, Agent, or Firm*—Roger A. Williams

[57] ABSTRACT

This invention relates to compounds of Formula I and the stereoisomers and pharmaceutically acceptable salts thereof

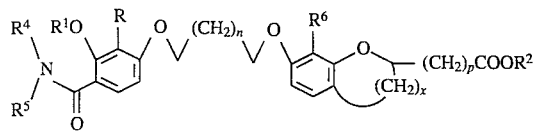

wherein
  R is alkyl, alkenyl, alkynyl, or cycloalkylalkyl;
  $R^1$ is alkyl;
  $R^2$ is hydrogen, alkyl;
  $R^6$ is alkyl;
  n is 1 to 5;
  p is 0 to 6;
  x is 0 or 2; and
  $R^4$ and $R^5$ are independently hydrogen or alkyl or together with N form a cycloalkylamine.

The compounds of Formula I are leukotriene $B_4$ antagonists and are useful as anti-inflammatory agents and in treating disease conditions mediated by $LTB_4$.

1 Claim, No Drawings

LEUKOTRIENE B₄ ANTAGONISTS

This is a divisional Application of application Ser. No. 08/205,909, filed on Mar. 3, 1994, now U.S. Pat. No. 5,439,839, which is a divisional application of U.S. Ser. No. 07/995,859, filed Dec. 23, 1992, now U.S. Pat. No. 5,310,951, which is a continuation-in-part of inactive prior PCT International application Ser. No. US91/04386 filed on Jun. 27, 1991, which is a continuation-in-part of U.S. Ser. No. 07/545,430, filed Jun. 28, 1990, now U.S. Pat. No. 5,124,350.

BACKGROUND OF THE INVENTION

1. Field of the Invention

This invention is in the field of pharmaceutical agents which selectively act as leukotriene $B_4$ ($LTB_4$) antagonists and are useful in treating leukotriene $B_4$ mediated diseases.

2. Prior Art

Leukotriene $D_4$ and $C_4$ ($LTD_4/LTC_4$) and leukotriene $B_4$ ($LTB_4$) are products of the arachidonic acid metabolic pathway. $LTD_4$ and $LTC_4$ are associated with smooth muscle contraction and contract guinea pig ileum, human and guinea pig bronchi and human pulmonary artery and vein. $LTB_4$ is associated with neutrophil activation and is characterized by chemotaxis, aggregation and degranulation. $LTB_4$ is believed to be an important mediator of inflammation. High levels of $LTB_4$ are detected in rheumatoid arthritis, gout, psoriasis, and inflammatory bowel disease. Thus antagonists of $LTB_4$ are useful in the therapy of such diseases.

*Gastroenterology*, 1985: 88: 580–7 discusses the role of arachidonic acid metabolites in inflammatory bowel disease.

*British Medical Bulletin*, (1983), vol. 39, No. 3, pp. 249–254, generally discusses the pharmacology and pathophysiology of leukotriene $B_4$.

*Biochemical and Biophysical Research Communications*, Vol. 138, No. 2 (1986), pp. 540–546 discusses the pharmacology of a specific $LTB_4$ antagonist which has a different structure than compounds of this invention.

U.S. Pat. No. 4,889,871 discloses alkoxy-substituted dihydrobenzopyran-2-carboxylate derivatives which are selective antagonists of $LTB_4$ with little or no antagonism of $LTD_4$ and are useful as antiinflammatory agents for treating inflammatory bowel disease. The compounds differ structurally from the compounds of this invention.

BRIEF DESCRIPTION OF THE INVENTION

This invention encompasses compounds of Formula I and the stereoisomers and pharmaceutically acceptable salts thereof;

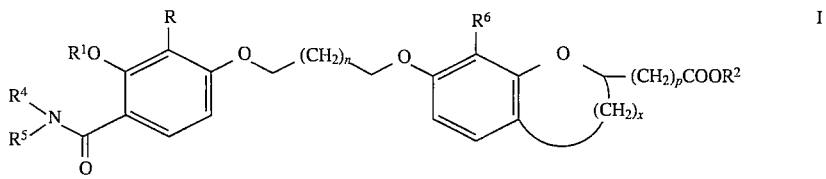

wherein

R represents alkyl having 1 to 6 carbon atoms, alkenyl having 2 to 6 carbon atoms, alkynyl having 2 to 6 carbon atoms, or $-(CH_2)_m-R^3$ wherein $R^3$ represents cycloalkyl of 3 to 5 carbons atoms and m is 1 or 2;

$R^1$ represents alkyl having 1 to 4 carbon atoms;

$R^2$ represents hydrogen alkyl having 1 to 5 carbon atoms;

$R^6$ represents alkyl having 1 to 6 carbon atoms;

n is an integer from 1 to 5;

p is an integer from 0 to 6;

x is 0 or 2; and $R^4$ and $R^5$ are independently hydrogen or alkyl having 1 to 4 carbon atoms, or $R^4$ and $R^5$ together with N form a cycloalkylamine having 4 to 5 carbon atoms.

The invention herein also includes compounds of the following structural formula wherein like components have the above definitions.

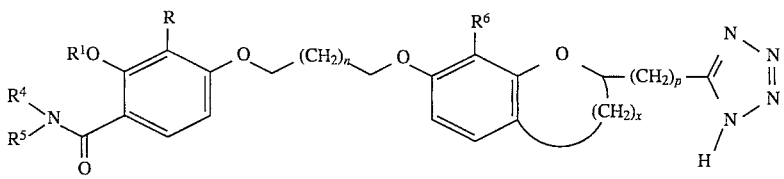

These compounds are selective antagonists of leukotriene $B_4$ ($LTB_4$) with little or no antagonism of leukotriene $D_4$ ($LTD_4$) and are useful anti-inflammatory agents for treating inflammatory bowel disease, rheumatoid arthritis, gout, asthma, psoriasis and multiple sclerosis and in treating diseases mediated by $LTB_4$.

DETAILED DESCRIPTION OF THE INVENTION

This invention encompasses the compounds of formula I as previously described.

Preferred embodiments of the present invention are compounds of the formula Ia, the stereoisomers and pharmaceutically acceptable salts thereof,

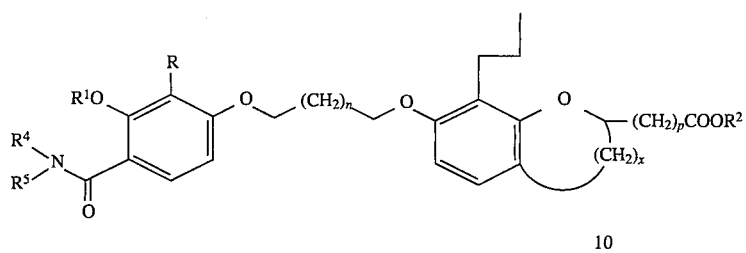

Ia wherein
R represents alkyl having 1 to 4 carbon atoms alkenyl having 3 to 4 carbon atoms, or cyclopropylalkyl wherein the alkyl moiety has 1 to 2 carbon atoms;

$R^1$ represents methyl or ethyl;

$R^2$ represents hydrogen alkyl having 1 to 3 carbon atoms;

n is an integer from 1 to 3;

p is an integer from 0 to 4;

x is 0 or 2; and $R^4$ and $R^5$ are independently hydrogen or alkyl having 1 to 4 carbon atoms or, $R^4$ and $R^5$ together with N form a cycloalkyl amine having 4 to 5 carbon atoms.

These compounds are selective antagonists of leukotriene $B_4$ ($LTB_4$) with little or no antagonism of leukotriene $D_4$ ($LTD_4$) and are useful anti-inflammatory agents for treating inflammatory bowel disease, rheumatoid arthritis, gout, asthma, multiple sclerosis, and psoriasis.

More preferred embodiments are compounds of the formula II and the stereoisomers and pharmaceutically acceptable salts thereof

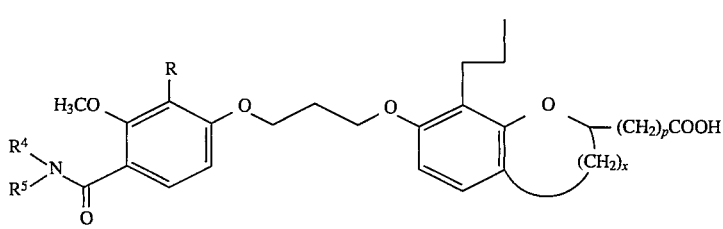

II wherein

R represents propyl, 2-propenyl, or cyclopropylmethyl;
p is an integer from 0 to 2; x is 0 or 2; and
$R^4$ and $R^5$ are independently hydrogen or alkyl having 1 to 4 carbon atoms or $R^4$ and $R^5$ together with N form a pyrrolidine ring. Included in the present invention are compounds of the formulas III and IV and the stereoisomers and pharmaceutically acceptable salts thereof

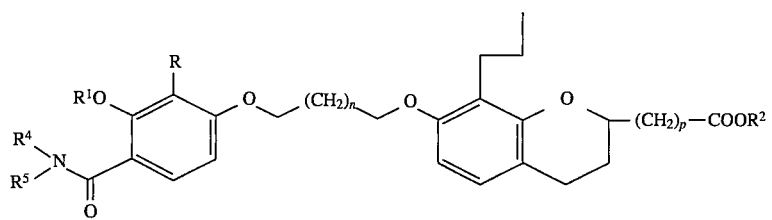

III

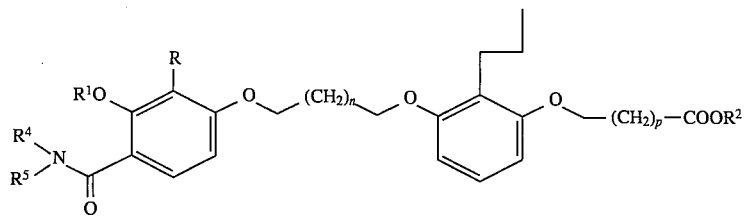

IV wherein
R represents alkyl having 1 to 4 carbon atoms, alkenyl having 3 to 4 carbon atoms, or cyclopropylalkyl wherein the alkyl moiety has 1 to 2 carbon atoms;

$R^1$ represents methyl or ethyl;

$R^2$ represents hydrogen or alkyl having 1 to 3 carbon atoms;

n is an integer from 1 to 3;

p is an integer from 0 to 4; and $R^4$ and $R^5$ are independently hydrogen or alkyl having 1 to 4 carbon atoms or $R^4$ and $R^5$ together with N form a cycloalkyl amine having 4 to 5 carbon atoms.

Preferred compounds are compounds of formulas IIIa and IVa and the stereoisomers and pharmaceutically acceptable salts thereof IIIa IVa wherein R represents propyl, 2-propenyl, or cyclopropylmethyl;

p is an integer from 0 to 2; and $R^4$ and $R^5$ are independently hydrogen or alkyl having 1 to 4 carbon atoms or $R^4$ and $R^5$ together with N form a pyrrolidine ring.

Alkyl defined for R, $R^1$, $R^2$, $R^4$, $R^5$, and $R^6$, is straight or branched chain alkyl having the indicated number of carbon atoms. Alkenyl defined for R is straight or branched chain alkenyl having the indicated number of carbon atoms. The term cycloalkyl includes cyclopropyl, cyclobutyl, and cyclopentyl.

Pharmaceutically acceptable salts such as ammonium, sodium, potassium, alkaline earth, tetraalkylammonium and the like are encompassed by the invention.

Scheme A shows a general method for preparing compounds of the invention. A 2,4-dihydroxy benzamide (V) is reacted with an alkyl 3,4-dihydro-7-(3-halopropoxy)-8-alkyl-2H-1-benzopyran-2-alkanoate (VI) in the presence of potassium carbonate and DMF. Reaction of VII with methyl iodide in DMF or dimethyl sulfate and potassium hydroxide gives the 3-alkoxy compound (VIII). Reaction of VIII with lithium hydroxide, methanol and water gives the final product IX. Pharmaceutically acceptable salts may be prepared from the acids by reacting them with an appropriate base.

Scheme B shows methods for the preparation of the 2,4-dihydroxybenzamide starting materials. Methyl 2,4-dihydroxybenzoate (X) is reacted with allyl bromide to give methyl 2-hydroxy-4-allyloxybenzoate (XI) which is heated to produce methyl 2,4-dihydroxy-3-(2-propenyl) benzoate (XII). Reaction of XII with an appropriate amine in the presence of ammonium chloride gives the 2,4-dihydroxy-3-(2-propenyl)benzamide (XIII) which can be hydrogenated to the 3-propyl compound (XIV). Alternatively XII may be reacted with methylene iodide and triisobutylaluminum to give methyl 3-(cyclopropylmethyl)-2,4-dihydroxybenzoate (XV) which is then reacted with an appropriate amine in the presence of ammonium chloride to give the 2-(cyclopropylmethyl)-2,4-dihydroxybenzamide (XVI).

Scheme C is a reaction scheme illustrating how the tetrazole compounds of the invention herein can be synthesized from the carboxylic acids.

Scheme A

V

VI

K₂CO₃/DMF

-continued
Scheme A
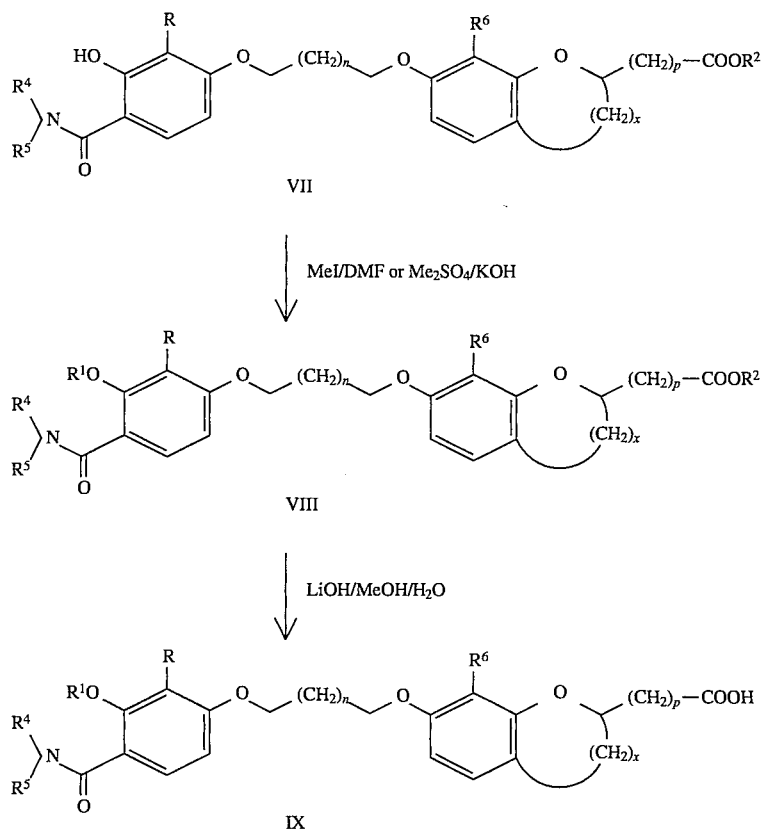
R, $R^1$, $R^2$, $R^4$, $R^5$, $R^6$ defined as hereinbefore
n = 1–7
p = 0–6
x = 0 or 2
W = Br, I
Scheme B
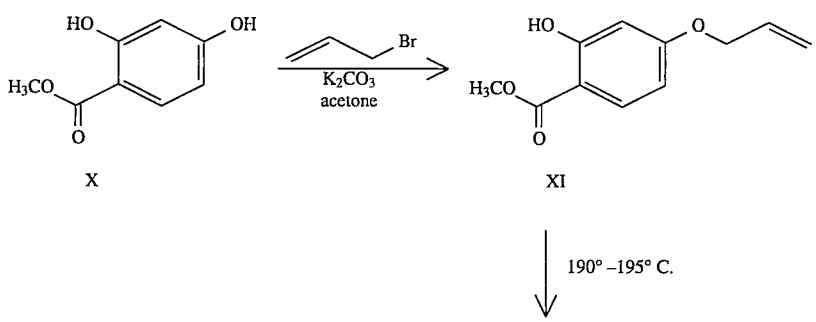

-continued
Scheme B
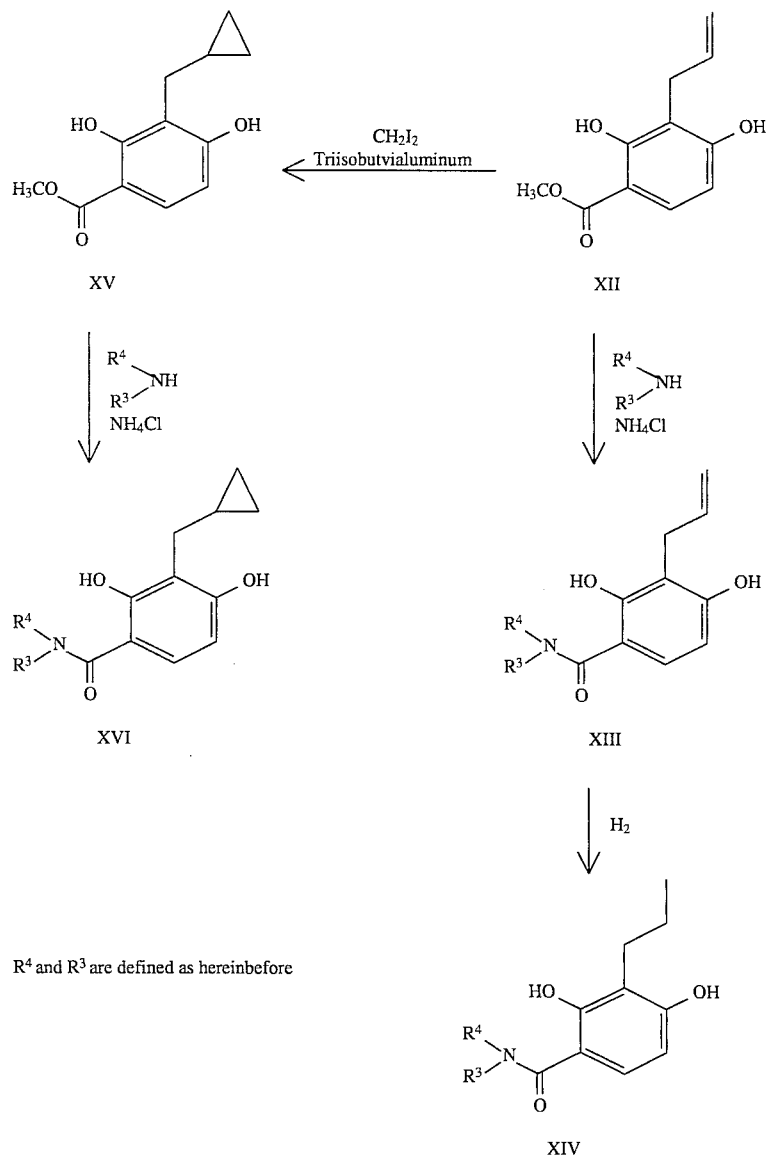
R⁴ and R³ are defined as hereinbefore

Scheme C
Scheme for Synthesis of Tetrazoles

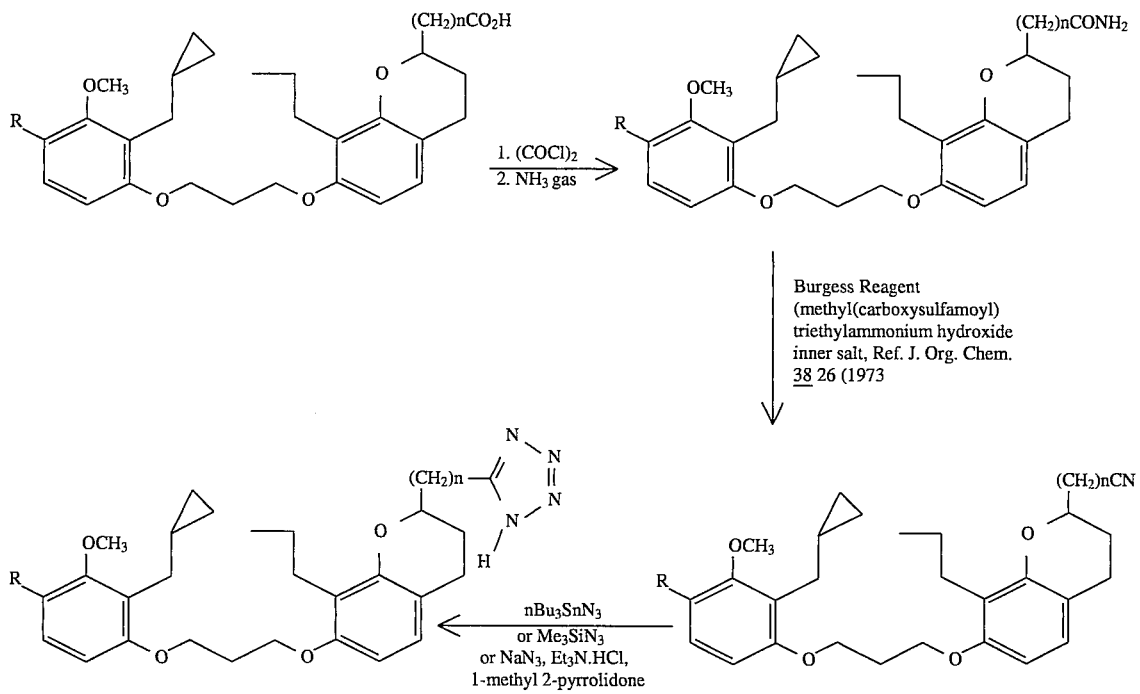

The biological activity of compounds of this invention is indicated by the following tests.

Preparation of Human Neutrophils

Neutrophils were purified from venous blood of normal human donors using standard techniques of dextran sedimentation, centrifugation on Ficoll-paque® (Pharmacia) or Histopaque® sterile solution (Sigma) and hypotonic lysis of erythrocytes (Boyum, A., *Isolation of Leukocytes From Human Blood: Further Observations. Scand. J. Lab. Clin. Invest.*, 21 (Suppl. 97): 31, 1968). The purity of isolated neutrophils was >95%.

LTB$_4$ Receptor Binding Assay

Neutrophils (4–6×10$^6$) in 1 ml Hanks' balanced salt solution (HBSS) containing 10 mM HEPES buffer, pH 7.4 and 20 mM nordihydroguaiaretic acid were incubated with 0.6×10$^{-9}$M ($^3$H) LTB$_4$ in the presence or absence of test compounds. The incubation was carried out at 0° C. for 45 minutes and terminated by adding 5 ml of ice-cold HBSS followed by rapid filtration of the incubation mixture under vacuum through GF/C glass fiber filters. The filters were further washed with 10 ml HBSS and radioactivity was determined. Specific binding was defined as the difference between total binding and nonspecific binding which was not displaced by 10$^{-7}$M unlabeled LTB$_4$. All data refer to specific binding.

Modified Boyden Chamber Chemotaxis

Human neutrophils were isolated from citrated peripheral blood using standard techniques of dextran sedimentation, followed by centrifugation on Histopaque® sterile solution (Sigma) or Ficoll-paque® (Pharmacia) and hypotonic lysis of erythrocytes. A final cell suspension of 3.4×10$^6$ neutrophils/ml of HEPES-buffered Hanks' balanced salt solution (HBSS, pH 7.3) was added to the upper well (0.8 ml) of a modified Boyden chamber (blind well). The lower well (0.2 ml), separated by a polycarbonate membrane (Nucleopore Corp.), contained HBSS or 3×10$^{-8}$M LTB$_4$ in the presence or absence of test compound. Following a 40–90 minute incubation at 37° C. in 5% CO$_2$-95% air, cells from the lower well were lysed and nuclei counted in a Model S-Plus-IV Coulter Counter. The number of neutrophils migrating into the lower chamber in the absence of chemoattractant was subtracted from the number of cells migrating in the presence of a chemoattractant. Inhibition of chemotaxis by test compounds was expressed as percent inhibition relative to uninhibited control.

Results for representative compounds of the invention are shown in Table 1.

Data are expressed as potency relative to the compound of Example 1(b), 7-[3,(4-acetyl-3-methoxy-2-propylphenoxy)propoxy]-3,4-dihydro-8-propyl-2H-1-benzopyran-2-carboxylic acid, which is disclosed in U.S. Pat. No. 4,889,871.

TABLE 1

Relative Potency Values for LTB$_4$ Antagonists [1]

| Compound | LTB$_4$ Receptor Binding | Chemotaxis | |
|---|---|---|---|
| | | LTB$_4$ | fMLP |
| Example 1(b) | 1.0 (0.3 µM) | 1.0 (1.8 µM) | 1.0 (5.4 µM) |
| Example 9 | 8.9 | 12.3 | 0.38 |
| Example 14 | 4.0 | 4.1 | 0.52 |
| Example 19 | 5.3 | 16.9 | 1.57 |
| Example 26 | 2.1 | 7.6 | 0.95 |
| Example 29 | 1.0 | 0.18 | — |
| Example 32 | 2.1 | 4.0 | 1.5 |
| Example 35 | 0.81 | 2.6 | — |
| Example 43 | 0.83 | 1.1 | ≦0.63 |
| Example 46 | 0.71 | 0.58 | ≦0.048 |
| Example 50 | 0.04 | 0.05 | <0.48 |
| Example 56 | 1.0 | 2.6 | <0.63 |
| Example 59 | 0.04 | <0.9 | — |
| Example 62 | 8.5 | 17.4 | 0.69 |

[1] Data are expressed as potency relative to a known LTB$_4$ antagonist, the compound of Example 1(b), defined as 1.0. Values in the parentheses refer to IC$_{50}$ values (µM) for the compound of Example 1 (b). IC$_{50}$ is the effective concentration needed to cause 50% inhibition.

The compounds of this invention can be administered in a number of dosage forms. A preferred method of delivery would be oral or in such a manner so as to localize the action of the antagonist. In an inflammatory condition such as rheumatoid arthritis the compounds could be injected directly into the affected joint. The compounds could also be administered in oral unit dosage forms such as tablets, capsules, pills, powders or granules. They may be introduced intraperitoneally, subcutaneously, or intramuscularly using forms known to the pharmaceutical art. Topical application in the form of salves and ointments are useful for treating psoriasis. Regardless of the route of administration selected, the compounds are formulated into pharmaceutically acceptable dosage forms by conventional methods known to the pharmaceutical art.

The compounds may be administered in a number of dosage forms, for example, such oral dosage forms as tablets, capsules, pills, powders, or granules. They may also be administered intravascularly, intraperitoneally, subcutaneously, topically or intramuscularly using forms known to the pharmaceutical art.

In general, a unit dosage of a compound of the invention would contain from about 50 mg to about 500 mg of the active ingredient with from about 70 mg to about 400 mg preferred. An effective but non-toxic quantity of the compound is employed in treatment. The dosage regimen for inhibition of $LTB_4$ by the compounds of this invention is selected in accordance with a variety of factors including the type, age, weight, sex, and medical condition of the mammal, the particular disease and its severity, the route of administration and the particular compound employed. An ordinarily skilled physician or veterinarian will readily determine and prescribe the effective amount of the compound to prevent or arrest the progress of the condition. In so proceeding, the physician or veterinarian could employ or use relatively low dosages at first, subsequently increasing the dose until a maximum response is obtained. Generally, a dosage range of 1 to 25 mg/kg of body weight is administered to patients in need of treatment for inflammatory conditions.

The following examples illustrate the preparation of compounds of this invention from known starting materials. The invention, which is set forth in the foregoing disclosure, is not to be construed or limited either in spirit or in scope by these examples. Those skilled in the art will readily understand that known variations of the conditions and processes of the following preparative procedures can be used to prepare these compounds. All temperatures are degrees Celsius unless otherwise noted.

U.S. Pat. No. 4,665,203 issued May 12, 1987, incorporated herein by reference, U.S. Pat. No. 4,889,871 issued Dec. 26, 1989, incorporated herein by reference, and European Application EP 0292977 published Nov. 30, 1988 disclose methods for making some of the intermediates used in making compounds of the present invention.

Example 1

(a) Methyl 7-[3-(4-acetyl-3-methoxy-2-propylphenoxy) propoxy]-3,4-dihydro-8-propyl-2H-1-benzopyran-2-carboxylate Methyl 7-[3-(4-acetyl-3-hydroxy-2-propyl-phenoxy)propoxy]-3,4-dihydro-8-propyl-2H-1-benzopyran-2-carboxylate (493 mg) was added to 25 ml of acetone containing 276 mg of anhydrous potassium carbonate and 282 mg of methyl iodide. The mixture was refluxed for about 24 hours and water was added and the mixture was then extracted with ethyl acetate. The extract was dried, the solvent removed under vacuum, and the residual oil was chromatographed over silica gel with a 40/60 mixture of ethyl acetate/hexane to provide pure methyl ether, methyl 7-[3-(4-acetyl-3-methoxy- 2-propylphenoxy)propoxy]-3,4-dihydro- 8-propyl-2H-1-benzopyran-2-carboxylate.

EXAMPLE 1(b)

7-[3-(4-acetyl-3-methoxy-2-propylphenoxy)propoxy]-3,4-dihydro- 8-propyl-2H-1-benzopyran-2-carboxylic acid

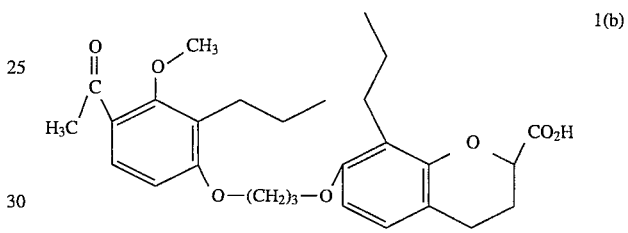

1(b)

(b) The methyl ether (1a) (340 mg) was dissolved in methanol (5 ml) containing lithium hydroxide (0.7 ml of a 2N LiOH solution in water). The mixture was stirred at room temperature overnight and the solvent removed in vacuo. The residue was partitioned between ethyl acetate and 2N HCl and the organic layer separated and washed with brine. Evaporation of the volatiles in vacuo afforded crude acid of Formula III. This material was purified by silica gel chromatography using ethyl acetate/hexane/acetic acid (40:60:0.5) as eluent. The pure product was recrystallized from ethyl acetate/hexane to afford 200 mg of product, 7-[3-(4-acetyl-3-methoxy-2-propylphenoxy) propoxy]-3,4-dihydro-8-propyl-2H-1-benzopyran-2-carboxylic acid, m.p. 65°–68° C.

Microanalysis: Found: C 69.22, H 7.53. Theory: C 69.40, H 7.49.

The NMR (CDCl$_3$) shows a —OCH$_3$ at δ3.75.

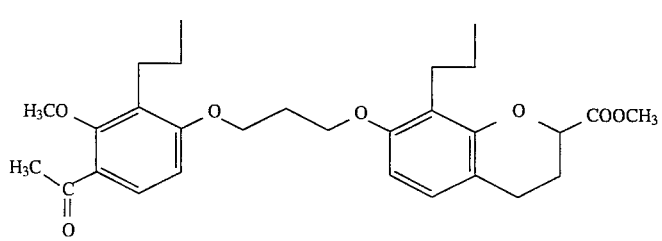

1a

EXAMPLE 2

Methyl 7-(3-chloropropoxy)-3,4-dihydro- 8-propyl-2-H-1-benzopyran-2-propanoate

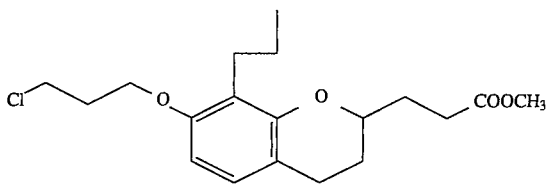

Methyl 7-(3-chloropropoxy)-4-oxo-8-propyl-4-H-1-benzopyran-2-propanoate (2.0 g, 5.35 mmol) was dissolved in a mixture of 25 ml ethyl acetate and 0.32 ml phosphoric acid and hydrogenated at 5 psi and 25° C. using 2 g of 5% Pd/C as catalyst. The product was dissolved in ethyl acetate, washed with 10% sodium carbonate solution, then washed once with water, dried over magnesium sulfate and filtered. The solvent was removed under vacuum to give the product as a colorless oil (1.5 gm, 90% yield).

EXAMPLE 3

Methyl 3,4-dihydro-7-(3-iodopropoxy)-8-propyl-2-H-1-benzopyran-2-propanoate

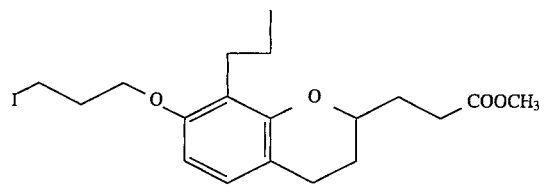

The compound of Example 2 (1.6 g, 4.521 mmol) was mixed with sodium iodide (6.8 g, 45.21 mmol) and methyl ethyl ketone (100 ml). The reaction mixture was stirred and refluxed overnight. The solvent was removed under vacuum and 100 ml of water was added to the residue. The solution was extracted three times with ethyl acetate. The extracts were combined, filtered, dried over magnesium sulfate and the solvent was removed under vacuum to give the product as a brown oil.

EXAMPLE 4

Methyl 2-hydroxy-4-allyloxybenzoate

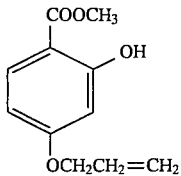

Methyl 2,4-dihydroxybenzoate (25 g, 148.7 mmol), allyl bromide (18.2 g, 150 mmol), and potassium carbonate (30.8 g, 22.3 mmol) were added to about 250 ml of acetone and the reaction mixture was refluxed with stirring overnight. The reaction mixture was filtered and concentrated. Separation of the pure compound was achieved by chromatography on silica gel using a Waters Prep 500™ and a 20% ethyl acetate/80% hexane solvent system.

EXAMPLE 5

Methyl 2,4-dihydroxy-3-(2-propenyl)benzoate

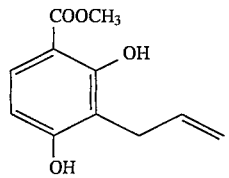

The product of Example 4 (10 g) was heated neat at 190–195° C. overnight, cooled and purified by chromatography on silica gel using 10% ethyl acetate/90% hexane as eluant to give the title compound (6.6 g, 66%).

EXAMPLE 6

2,4-Dihydroxy-N-methyl-3-(2-propenyl)benzamide

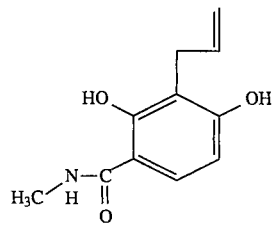

The compound of Example 5 (3.5 g) and excess methyl amine (40% aqueous solution) were stirred overnight at 50° C. in the presence of a few crystals of ammonium chloride. The reaction mixture was cooled and neutralized with 10% hydrochloric acid then extracted with ethyl acetate. The organic layer was dried over magnesium sulfate and concentrated under vacuum. The crude crystals were dissolved in chloroform and then hexane was added until the product precipitated out of solution. The precipitate was filtered and dried to give the product (2.5 g, 75% yield).

Analysis calculated for $C_{11}H_{13}NO_3$. Calculated: C, 63.76; H, 6.32; N, 6.76 Found : C, 63.32; H, 6.43; N, 6.60

EXAMPLE 7

Methyl 3,4-dihydro-7-[3-[3-hydroxy-4-[(methylamino)carbonyl]-2-(2-propenyl)phenoxy]propoxy]-8-propyl-2-H-1-benzopyran-2-propanoate

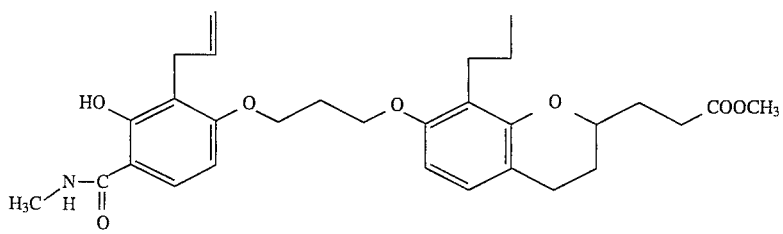

The compound of Example 6 (465 mg), the compound of Example 3 (1 g) and potassium carbonate (312 mg) were added to 5.0 ml of dimethylformamide (DMF), and the reaction mixture was stirred at room temperature for about 2 days. Water (20 ml) was added and the reaction mixture was extracted three times with ethyl acetate and the combined extracts washed twice with water, dried and filtered. Solvent was removed under vacuum to give an oil. Chromatography of the oil on silica gel with 20/80 ethyl acetate/hexane gave the product as a white solid.

Analysis calculated for $C_{30}H_{39}NO_7$ (525.64) Calculated: C, 68.55; H, 7.48; N, 2.56 Found : C, 68.42; H, 7.60; N, 2.70

EXAMPLE 8

Methyl 3,4-dihydro-7-[3-[3-methoxy-4-[(methylamino)carbonyl]-2-(2-propenyl)phenoxy]propoxy]-8-propyl-2-H-1-benzopyran-2-propanoate

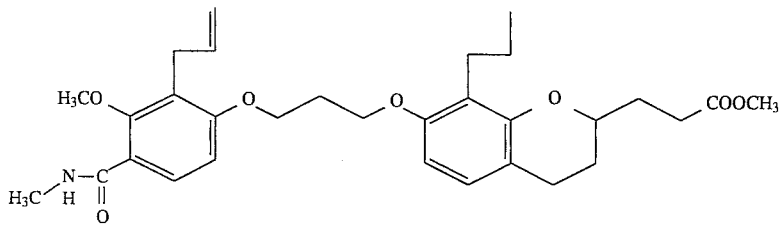

The compound of Example 7 (260 mg, 0.4946 mmol) was added to 2.0 ml of tetrahydrofuran (THF). Potassium hydroxide (33.3 mg, 0.5935 mmol) was added and the reaction mixture was stirred for five minutes at room temperature. Dimethyl sulfate (93.6 mg, 0.7419 mmol) was added, and the reaction mixture was stirred at room temperature overnight. After the addition of 10 ml of water the reaction mixture was extracted three times with ethyl acetate. The combined extracts were dried and filtered and the solvent was removed under vacuum to give the product as an oil.

EXAMPLE 9

3,4-Dihydro-7-[3-[3-methoxy-4-[(methylamino) carbonyl]-2-(2-propenyl)phenoxy]propoxy]-8-propyl-2-H-1-benzopyran-2-propanoic acid

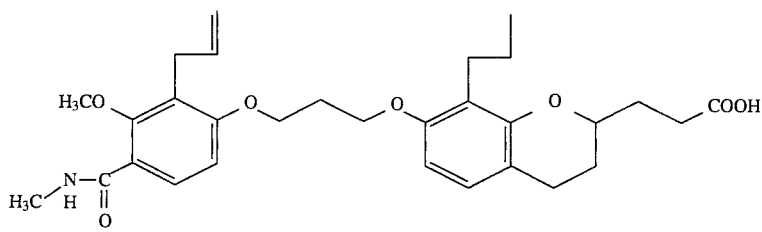

The compound of Example 8 (250 mg, 0.4629 mmol) was dissolved in 2.0 ml of methanol and 694 µl of 1M lithium hydroxide was added. The reaction mixture was stirred at room temperature for about two days. The solvent was removed under vacuum and 20 ml of water was added. The aqueous residue was acidified with 10% hydrochloric acid. Filtration of the resultant suspension yielded the product as white solid.

Analysis calculated for $C_{30}H_{39}NO_7$ (527.898) Calculated: C, 68.25; H, 7.48; N, 2.65 Found: C, 68.00; H, 7.47; N, 2.57

EXAMPLE 10

2,4-Dihydroxy-N-methyl-3-propylbenzamide

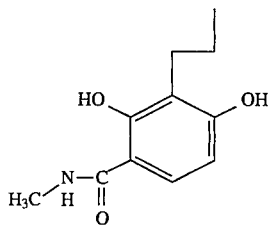

The compound of Example 6 (1.0 g) was dissolved in 30 ml of ethanol and hydrogenated at room temperature and 5 psi for 2 hours and 25 minutes using 200 mg of 4% Pd/C as catalyst. The solvent was removed under vacuum to give the product as a white solid.

EXAMPLE 11

Ethyl 3,4-dihydro-7-(3-iodopropoxy)-8-propyl-2H-1-benzopyran-2-propanoate

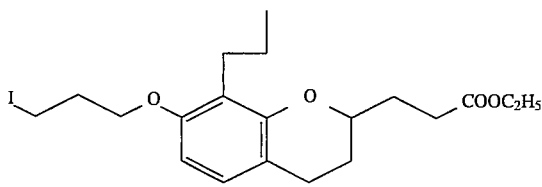

Ethyl 7-(3-chloropropoxy)-3,4-dihydro-8-2H-1-benzopyran-2-propanoate (3.2 g, 9.042 mmol) and sodium iodide (13.6 g, 9.042 mmol) were added to 200 ml of methyl ethyl ketone and the reaction mixture was heated to reflux overnight. The solvent was removed under vacuum and 100 ml of water was added. The solution was extracted 3 times with ethyl acetate. The combined extracts were dried and filtered, and the solvent was removed under vacuum to give the product as a brown oil.

EXAMPLE 12

Ethyl 3,4-dihydro-7-[3-[3-hydroxy-4-[(methylamino) carbonyl]-2-propylphenoxy]propoxy]-8-propyl-2H-1-benzopyran- 2-propanoate

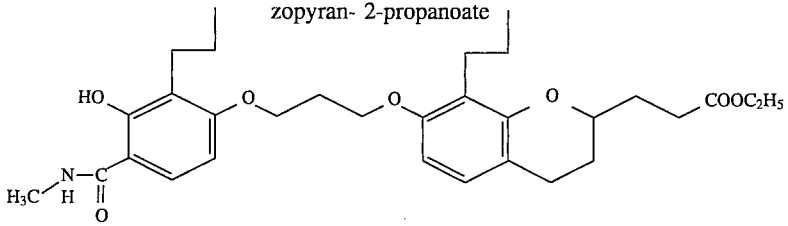

The compound of Example 10 (418 mg, 2.0 mmol), the compound of Example 11 (895 mg, 2.0 mmol), and potassium carbonate (552 mg, 4.0 mmol) were added to 3.0 ml DNF, and the reaction mixture was stirred at room temperature overnight. The reaction mixture was partitioned between ethyl acetate and water. The organic layer was separated, washed with water, and dried over magnesium sulfate. Evaporation of the volatiles afforded a crude oil which was purified by chromatography using 50/50 ethyl acetate/hexane as eluant to give the product as a white solid.

Analysis calculated for $C_{31}H_{43}NO_7$ (541.68) Calculated: C, 68.74; H, 8.00; N, 2.59 Found: C, 68.32; H, 8.11; N, 2.44

EXAMPLE 13

Ethyl 3,4-dihydro-7-[3-[3-methoxy-4-[(methylamino) carbonyl]-2-propylphenoxy]propoxy]-8-propyl-2H-1-benzopyran- 2-propanoate

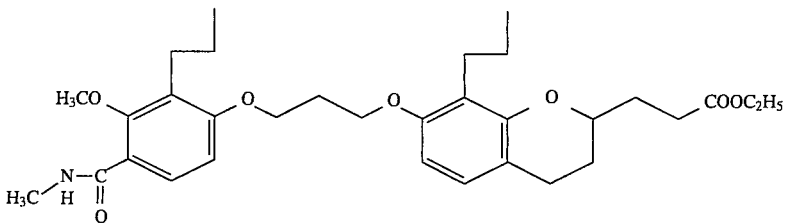

The compound of Example 12 (226 mg, 0.4172 mmol), potassium hydroxide (28 mg, 0.5006 mmol) and dimethyl sulfate (79 mg, 0.626 mmol) were added to 2.0 ml tetrahydrofuran (THF). The reaction mixture was stirred at room temperature overnight. Additional potassium hydroxide (10 mg) and dimethyl sulfate (20 mg) were added continued for four hours. Water (5.0 ml) was added, and the solution was extracted three times with ethyl acetate. The combined extracts were dried and filtered and the solvent was removed under vacuum to give an oil which was purified by chromatography on silica gel using 50/50 ethyl acetate/hexane as eluant to give the pure product.

EXAMPLE 14

3,4-Dihydro-7-[3-[3-methoxy-4-[(methylamino) carbonyl]-2-propylphenoxy]propoxy]-8-propyl-2H-1-benzopyran-2-propanoic acid

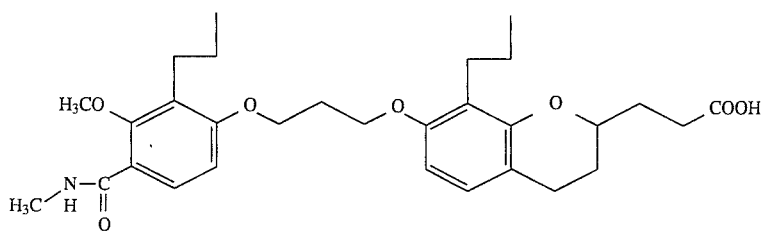

The compound of Example 13 (160 mg, 0.2877 mmol) was added to 2 ml of methanol and 432 μl of 1M lithium hydroxide was added. The reaction mixture was stirred at room temperature overnight. The solvent was removed under vacuum, water (5.0 ml) was added and the solution was acidified with 10% hydrochloric acid then extracted 3 times with ethyl acetate. The combined extracts were dried over anhydrous magnesium sulfate and filtered. The solvent was removed under vacuum to give a gum. Further drying under high vacuum overnight gave the product.

Analysis calculated for $C_{30}H_{41}NO_7 \cdot H_2O$ (545.67) Calculated: C, 66.03; H, 7.89; N, 2.57 Found : C, 66.13; H, 7.72; N, 2.51

EXAMPLE 15

Methyl 3-(cyclopropylmethyl)-2,4-dihydroxybenzoate

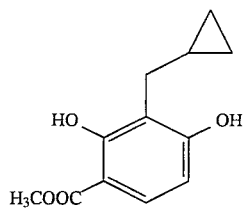

The compound of Example 5 (1.0 g, 4.8 mMol) was dissolved in methylene chloride (20cm³) and transferred to a 100 ml three-neck round bottom flask under an argon atmosphere at 0° C. Triisobutylaluminum (2.95 g, 3.76 ml, 14.9 mmol) was added dropwise via a dropping funnel. The reaction mixture was stirred for about 20 minutes while maintaining the temperature at 0° C., then methylene iodide (1.67 g, 0.5 ml, 6.2 mmol) was added via syringe, and the reaction mixture was stirred at room temperature for about four hours then slowly poured into an ice cold solution of 10% sodium hydroxide. The aqueous layer was extracted twice with about 25 ml of methylene chloride, and all of the organic fractions were combined, dried over magnesium sulfate and concentrated in vacuo to give the product.

EXAMPLE 16

3-(Cyclopropylmethyl)-2,4-dihydroxy-N-methylbenzamide

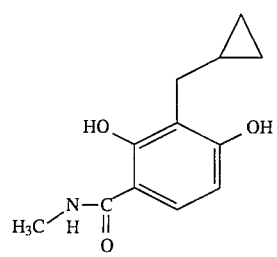

The compound of Example 15 (112 mg) was dissolved in about 5 to 10 ml of a 40% aqueous solution of methylamine. A few crystals of ammonium chloride were added, and the reaction mixture was stirred for about 6 hours at 50° C. The reaction mixture was neutralized with 10% hydrochloric acid and extracted with ethyl acetate. The organic layer was dried, concentrated, and chromatographed on silica gel using 15% ethyl acetate/85% hexane as eluant to give the product.

EXAMPLE 17

Methyl 7-[3-[2-(cyclopropylmethyl)-3-hydroxy-4-[(methylamino)carbonyl]phenoxy]propoxy]-3,4-dihydro-8-propyl-2H-1-benzopyran-2-carboxylate

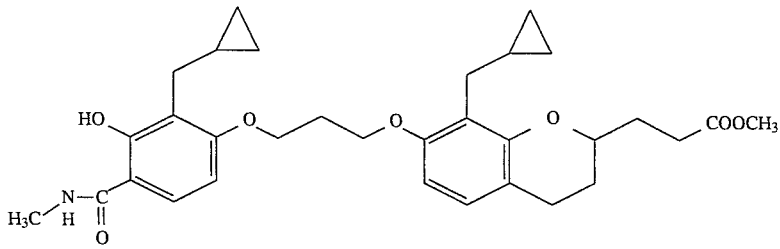

The compound of Example 16 (50 mg, 0.226 mmol), methyl 3,4-dihydro- 7-(3-iodopropoxy)-8-(2-propenyl)-2H-1-benzopyran-2-carboxylate (95 mg, 0.226 mmol), and potassium carbonate (78 mg, 0.565 mmol) were added to 10 ml of DMF, and the reaction mixture was stirred at room temperature overnight. The reaction mixture was washed with water and extracted with ethyl acetate then dried over magnesium sulfate and concentrated in vacuo to give the crude product. Chromatography of the crude product on silica gel using 15% ethyl acetate/85% hexane as eluant provided the product.

EXAMPLE 18

Methyl 7-[3-[2-(Cyclopropylmethyl)-3-methoxy-4-[(methylamino)carbonyl]phenoxy]propoxy]-3,4-dihydro-8-propyl-2H-1-benzopyran-2-carboxylate

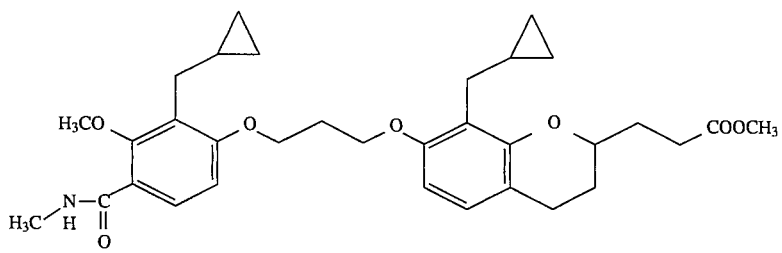

The compound of Example 17 (20 mg, 0.04 mmol), dimethyl sulfate (0.5 mg, 0.12 mmol), and potassium hydroxide (4.5 mg, 0.08 mmol) were added to about 5 ml of THF, and the reaction mixture was stirred overnight at room temperature. The reaction mixture was partitioned between ethyl acetate and water. The organic layer was separated, dried over magnesium sulfate, and concentrated in vacuo to give the product.

EXAMPLE 19

7-[3-[2-(Cyclopropylmethyl)-3-methoxy-4-[(methylamino)carbonyl]phenoxy]propoxy]-3,4-dihydro-8-propyl-2H-1-benzopyran-2-carboxylic acid

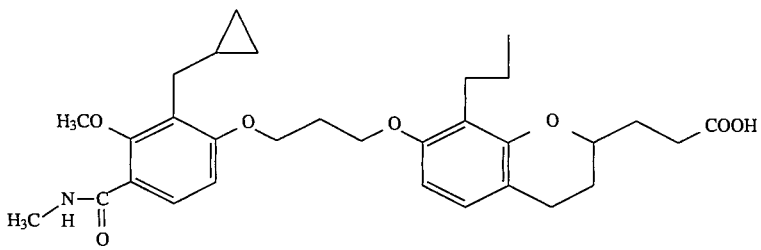

The compound of Example 18 (20 mg, 0.038 mmol) was added to 2 drops of 1M lithium hydroxide, about 2 ml of methanol and 1.0 ml of water. The reaction mixture was stirred overnight at room temperature then washed with water, extracted with ethyl acetate, dried over magnesium sulfate and concentrated to yield the crude product. Chromatography of the crude product on silica gel with 90% ethyl acetate, 10% methanol and a trace amount of acetic acid as eluant gave the product.

Analysis calculated for $C_{29}H_{37}NO_7$ (541.68) Calculated: C, 68.08; H, 7.29; N, 2.75 Found : C, 67.83; H, 7.21; N, 2.69

EXAMPLE 20

2,4-Dihydroxy-3-(2-propenyl)benzamide

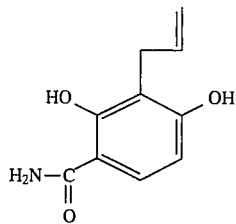

(a) Methyl 2,4-dihydroxy-3-(2-propenyl)benzoate (4.4 g) was added to a mixture of about 10 to 15 ml of saturated ammonium chloride solution and 2 to 3 ml of ethanol. The reaction mixture was stirred overnight at 50° C. The reaction mixture was extracted five times with ethyl acetate, and the organic layer was concentrated under vacuum. The product was crystallized and recrystallized from chloroform. Subsequent chromatography of the precipitated product on a 25 g silica gel column with 40% ethyl acetate/hexane as eluant gave the pure product.

EXAMPLE 21

1-[2,4-Dihydroxy-3-(2-propenyl)benzoyl]pyrrolidine

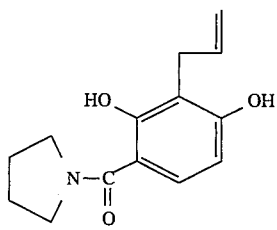

Methyl 2,4-dihydroxy-3-(2-propenyl)benzoate (3.0 g) and a few crystals of ammonium chloride were added to 20 ml of pyrrolidine. The reaction mixture was heated to 50° C. and stirred overnight. The reaction mixture was neutralized with 10% hydrochloric acid and extracted with ethyl acetate. Concentration under vacuum to remove solvent gave the product as a light brown solid.

EXAMPLE 22

Methyl 7-(3-chloropropoxy)-3,4-dihydro-8-propyl-2H-1-benzopyran-2-carboxylate

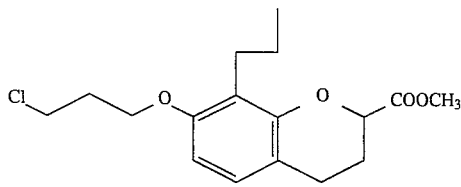

Methyl 3,4-dihydro-7-hydroxy-8-propyl-2H-1-benzopyran-2-carboxylate (10 g, 40 mmol), 1-bromo-3-chloropropane (75 g, 48 mmol), and potassium carbonate (828 g, 60 mmol) were added to 100 ml of methyl ethyl ketone, and the reaction mixture was heated to reflux and stirred overnight. The reaction mixture was diluted with ethyl acetate and washed with water. The organic layer was dried over magnesium sulfate, concentrated, and the crude product was chromatographed on silica gel using 20% ethyl acetate/80% hexane as eluant to give the product.

stirred overnight. The reaction mixture was filtered, and the filtrate was concentrated under vacuum to give light brown crystals. Recrystallization from methanol/hexane gave 700 mg of the product as light yellow crystals.

EXAMPLE 24

Methyl 3,4-dihydro-7-[3-[3-hydroxy-4-[(methylamino)carbonyl]-2-(2-propenyl)phenoxy]propoxy]-8-propyl-2H-1-benzopyran-2-carboxylate

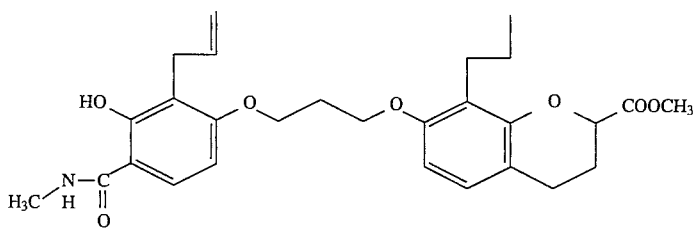

EXAMPLE 23

Methyl 7-(3-iodopropoxy)-3,4-dihydro-8-propyl-2H-1-benzopyran-2-carboxylate

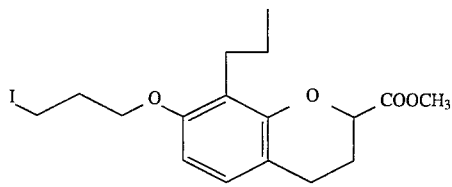

The compound of Example 23 (1.12 g, 5 mmol) and sodium iodide (1.21 g, 7.5 mmol) were added to about 15 to 20 ml of acetone. The reaction mixture was heated to reflux and 2,4-Dihydroxy-N-methyl-3-(2-propenyl)benzamide (770 mg, 3.7 mmol), the compound of Example 23 (650 mg, 1.55 mmol), and potassium carbonate (321 mg, 2.32 mmol) were added to about 20 ml of DMF, and the reaction mixture was stirred overnight at room temperature in a 100 ml pear-shaped flask. The reaction mixture was diluted with ethyl acetate and washed with water. The organic layer was dried over magnesium sulfate, concentrated under vacuum and chromatographed on silica gel using 40% ethyl acetate/hexane as eluant to give the product.

EXAMPLE 25

Methyl 3,4-dihydro-7-[3-[3-methoxy-4[(methylamino) carbonyl]-2-(2-propenyl)phenoxy]-8-propyl-2H-1-benzopyran-2-carboxylate

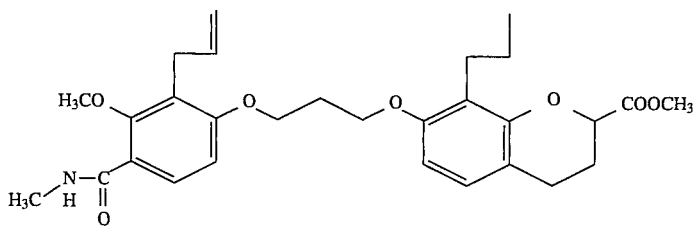

The compound of Example 24 (300 mg, 0.5 mmol), dimethyl sulfate (228 mg, 0.171 ml, 1.8 mmol) and potassium hydroxide (68 mg, 1.2 mmol) were added to about 20 ml THF. The reaction mixture was stirred overnight at room temperature and then washed with water and thoroughly extracted with ethyl acetate. The organic layer was dried over magnesium sulfate and concentrated in vacuo. Chromatography of the crude material on silica gel with 50% hexane/ethyl acetate as eluant gave the product.

Analysis calculated for: $C_{29}H_{37}NO_7$ Calculated: C, 68.08; H, 7.29; N, 2.74. Found : C, 67.78; H, 6.63; N, 2.37.

EXAMPLE 26

3,4-Dihydro-7-[3-[3-methoxy-4-[(methylamino) carbonyl]-2-(2-propenyl)phenoxy]propoxy]-8-propyl 2H-1-benzopyran-2-carboxylic acid

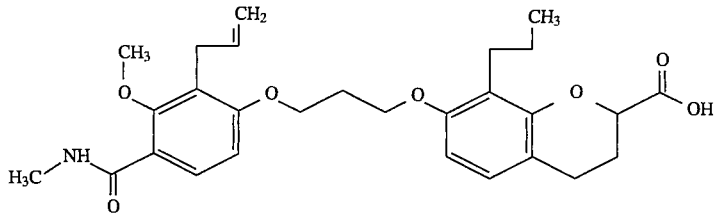

The compound of Example 25 (90 mg, 0.18 mmol) and an excess of 1M lithium hydroxide were added to 2 to 3 ml of methanol and about 10 ml of THF. The reaction mixture was stirred at room temperature overnight in a 50 ml pear-shaped flask. The reaction mixture was diluted with ethyl acetate and washed with water. Chromatography of the reaction mixture on silica gel with 90% ethyl acetate/9.5% methanol/0.5% acetic acid as eluant gave the product.

Analysis calculated for $C_{28}H_{35}NO_7$ (497.594) Calculated: C, 67.59; H, 7.09; N, 2.82 Found : C, 67.19; H, 7.08; N, 2.79.

EXAMPLE 27

Methyl-3,4-dihydro-7-[3-[3-hydroxy-2-(2-propenyl)-4-(1-pyrrolidinylcarbonyl)phenoxy]propoxy]-2-propyl-2H-1-benzopyran-2-carboxylate

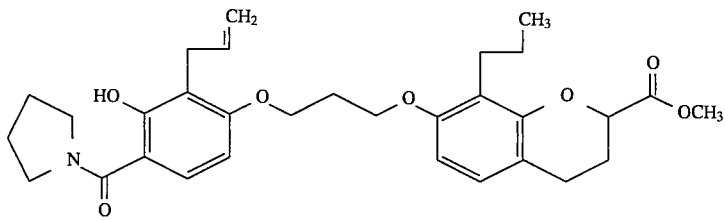

1-[2,4-Dihydroxy-3-(2-propenyl)benzoyl]pyrrolidine (260 mg, 1.05 mmol), the compound of Example 23 (440 mg, 1.05 mmol), and potassium carbonate (350 mg, 2.4 mmol) were added to about 15 to 20 ml of DMF, and the reaction mixture was stirred at room temperature overnight. The reaction mixture was diluted with ethyl acetate and washed with water. The organic layer was dried over magnesium sulfate and concentrated under vacuum. Chromatography of the crude material on silica gel using 20% ethyl acetate/hexane as eluant gave the product.

EXAMPLE 28

Methyl 3,4-dihydro-7-[3-[3-methoxy-2-(2-propenyl) 4-(1-pyrrolidinylcarbonyl)phenoxy]propoxy]-2H-1-benzopyran- 2-carboxylate

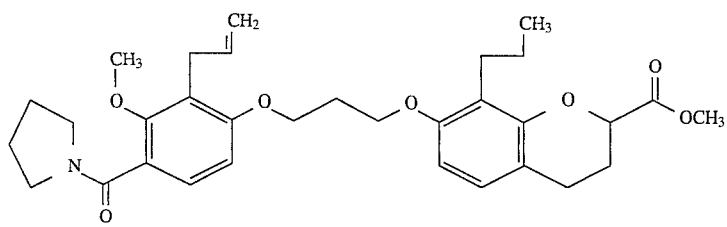

The compound of Example 27 (280 mg, 0.51 mmol) dimethyl sulfate (192 mg, 153 mmol) and potassium hydroxide (57 mg, 1 mmol) was added to about 20 ml of THF, and the reaction mixture was stirred overnight at room temperature. The reaction mixture was washed with water and thoroughly extracted with ethyl acetate. The organic layer was dried over magnesium sulfate and concentrated in vacuo. Chromatography of the crude material on silica gel using 75% ethyl acetate/hexane as eluant gave the product.

EXAMPLE 29

3,4-Dihydro-7-[3-[3-methoxy-2-(2-propenyl)-4-(1-pyrrolidinylcarbonyl)phenoxy]propoxy]-8-propyl-2H-1-benzopyran-2-carboxylic acid

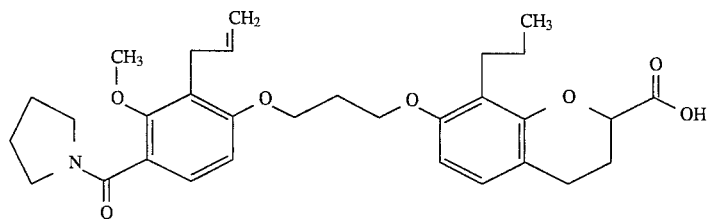

The compound of Example 27 (150 mg, 0.27 mmol) and an excess amount of lithium hydroxide were added to 2 to 3 ml of methanol and about 10 ml of THF. The reaction mixture was stirred overnight at room temperature. The reaction mixture was diluted with ethyl acetate and washed with water. Chromatography of the reaction mixture on silica gel with 90% ethyl acetate/9.5% methanol/0.5% acetic acid as eluant gave the product.

Analysis calculated for: $C_{31}H_{39}NO_7$ (537.659) Calculated: C, 69.25; H, 7.31; N, 2.60. Found: C, 69.31; H, 7.24; N, 2.31.

EXAMPLE 30

Methyl 7-[3-[4-(aminocarbonyl)-3-hydroxy-2-(2-propenyl)phenoxy]propoxy]-3,4-dihydro-8-propyl-2H-1-benzopyran-2-carboxylate

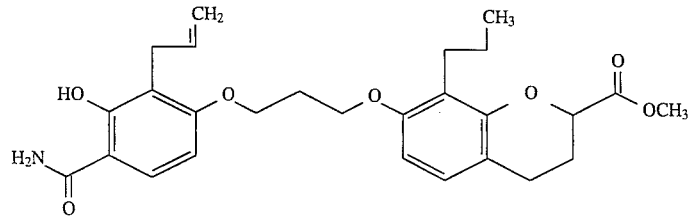

The compound of Example 20 (550 mg, 2.89 mmol), the compound of Example 23 (1.21 g, 2.89 mmol), and potassium carbonate (800 mg, 5.78 mmol) were added to about 25 to 30 ml of DMF. The reaction mixture as stirred at room temperature for 12 hours. The reaction mixture was diluted with ethyl acetate and washed with water. The organic layer was dried over magnesium sulfate and concentrated under vacuum. The crude material was chromatographed on silica gel with 30% ethyl acetate/hexane as eluant. The fractions containing the product were collected and the solvent was removed under vacuum to give the product as a white solid.

EXAMPLE 31

Methyl 7-[3-[4-(aminocarbonyl)-3-methoxy-2-(2-propenyl)phenoxy]propoxy]-3,4-dihydro-8-propyl-2H-1-benzopyran-2-carboxylate

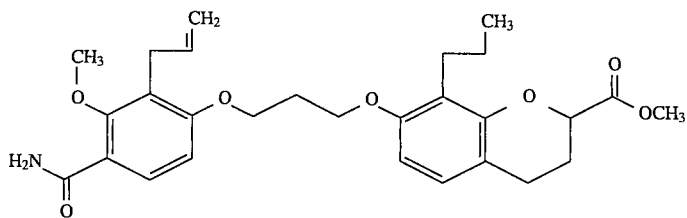

The compound of Example 30 (290 mg, 0.6 mmol), dimethyl sulfate (227 mg, 1.8 mmol) and potassium hydroxide (67 mg, 1.2 mmol) were added to abut 20 ml of THF in a 50 ml pear-shaped flask. The reaction mixture was stirred at room temperature for about 6 to 7 hours. The reaction mixture was diluted with ethyl acetate and washed with water. The organic layer was dried over magnesium sulfate and concentrated under vacuum. Chromatography of the crude material on silica gel with 90% ethyl acetate/hexane as eluant gave the product as pure white crystals, about 10 to 15 ml of THF. The reaction mixture was stirred overnight at room temperature, and then diluted with ethyl acetate and washed with water. The dried (MgSO$_4$) solvent was removed in vacuo and the residue was purified by chromatography on silica gel using 90% ethyl acetate/9.5% methanol/0.5% acetic acid as eluant to give the product.

Analysis calculated for: $C_{27}H_{33}NO_7$ (483.567) Calculated: C, 67.06; H, 6.88; N, 2.90. Found : C, 66.67; H, 6.80; N, 2.83.

EXAMPLE 33

Methyl 3,4-dihydro-7-[3-[3-hydroxy-2-propyl-4-[(methylamino)carbonyl]phenoxy]propoxy]-8-propyl-2H-1-benzopyran-2-carboxylate

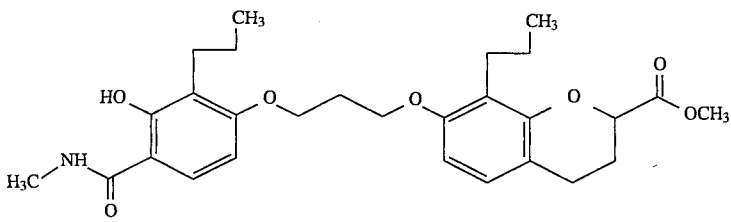

EXAMPLE 32

7-[3-[4-(Aminocarbonyl)-3-methoxy-2-(2-propenyl) phenoxy]propoxy]-3,4-dihydro-8-propyl-2H-1-benzopyran-2-carboxylic acid

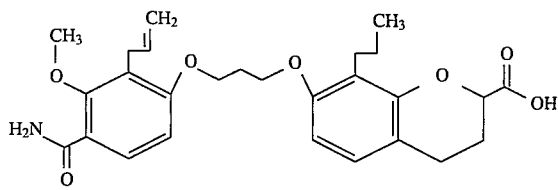

The compound of Example 31 (190 mg) and excess lithium hydroxide was added to about 2 to 3 ml of methanol and The compound of Example 10 (200 mg, 0.96 mmol), the compound of Example 23 (400 mg, 0.96 mmol) and potassium carbonate (264 mg, 1.92 mmol) were added to about 20 ml of DMF. The reaction mixture was stirred at room temperature overnight. The reaction mixture was diluted with ethyl acetate and washed with water. The organic layer was dried over magnesium sulfate and concentrated under vacuum, Chromatography of the crude material on silica gel with 30% ethyl acetate/hexane as eluant followed by rechromatography using the same solvent system gave the product.

EXAMPLE 34

Methyl 3,4-dihydro-7-[3-[3-methoxy-2-propyl-4-[(methylamino)carbonyl]phenoxy]propoxy]-8-propyl- 2H-1-benzopyran-2-carboxylate

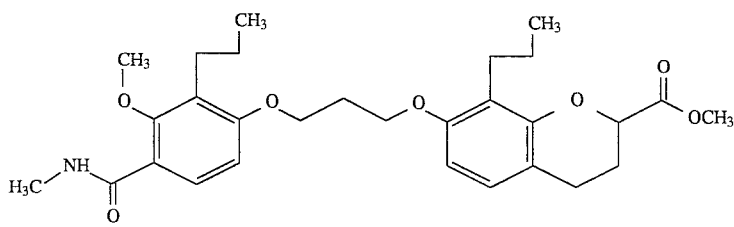

The compound of Example 33 (100 mg, 0.2 mmol), dimethyl sulfate (76 mg, 0.6 mmol), and potassium hydroxide (22 mg, 0.4 mmol) were added to about 15 ml of THF. The reaction mixture was stirred overnight at room temperature then washed with water and thoroughly extracted with ethyl acetate. The organic layer was dried over magnesium sulfate and concentrated in vacuo. Chromatography of the crude material on silica gel using 50/50 ethyl acetate/hexane as eluant gave the product.

EXAMPLE 35

3,4-Dihydro-7-[3-[3-methoxy-2-propyl-4-[(methylamino)carbonyl]phenoxy]propoxy]-8-propyl- 2H-1-benzopyran-2-carboxylic acid

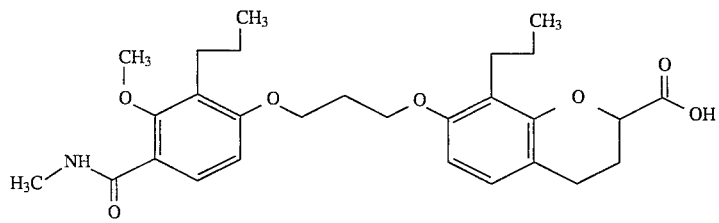

The compound of Example 34 (70 mg, 0.14 mmol) and excess 1.0M lithium hydroxide solution were added to about 2 ml of methanol and about 1 ml of THF. The reaction mixture was stirred at room temperature overnight and then diluted with ethyl acetate and washed with water. Chromatography of the reaction mixture on silica gel with 90% ethyl acetate/10% methanol/trace amount of acetic acid as eluant gave the product.

Analysis calculated for: $C_{28}H_{37}NO_7$ (499.61) Calculated: C, 67.31; H, 7.47; N, 2.80; Found: C, 67.26; H, 7.54; N, 2.82

EXAMPLE 36

2,4-Dihydroxy-3-propylbenzene

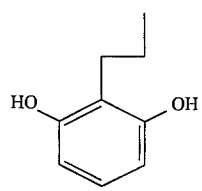

2,4,-Dimethoxy-3-propylbenzene (7.2 g, 39.94 mmol) was dissolved in 50 ml methylene chloride and the solution was cooled to −70° C. then 87.0 ml of 1M boron tribromide in methylene chloride was added over a period of 1 hour. The reaction mixture was stirred at −70° C. for 1 hour, then at room temperature for 2 hours. The reaction mixture was poured into 250 ml of ice water very slowly. This mixture was extracted 3 times with 100 ml methylene chloride. The extracts were combined, dried over anhydrous magnesium sulfate, filtered, and the solvent was removed under vacuum to give the product as a white solid (4.9 g, 81.7%).

Analysis calculated for $C_9H_2O_2$ (152.19) Calculated: C, 71.03; H, 7.95 Found: C, 70.99; H, 8.26

EXAMPLE 37

Ethyl (3-hydroxy-2-propylphenoxy)acetate

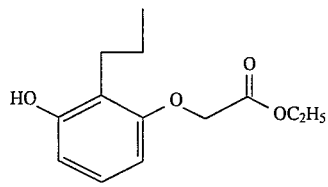

60% Sodium hydride in oil (1.66 g, 41.39 mmol) was washed with hexane. The hexane was decanted and 200 ml THF was added and the mixture was cooled to −10° C. The compound of Example 36 (6.0 g, 39.42 mmol) in 30 ml of THF was added dropwise. After the addition was complete, the reaction mixture was stirred at 0° C. for 30 min., then ethyl bromoacetate (7.2 g, 43.37 mmol) in 10 ml THF was added dropwise. After the addition was completed, the reaction mixture was stirred for 2 hours at 0° C. then overnight at room temperature. The reaction mixture was cooled in an ice water bath and 5.0 ml of water was added. The layers were separated and the aqueous solution was extracted with ethyl acetate three times. The combined organic extracts were dried over anhydrous magnesium sulfate, filtered and the solvent was removed under vacuum to give the crude product as an oil. Chromatography of the crude product on silica gel using 15/85 dioxane/1,1,1-trichlorotrifluoroethane as eluant gave the product (4.2 g).

Analysis calculated for $C_{13}H_{18}O_4$ (238.28) Calculated: C, 65.53; H, 7.61 Found: C, 65.68; H, 7.75

EXAMPLE 38

Ethyl [3-(3-chloropropoxy)-2-propylphenoxy]acetate

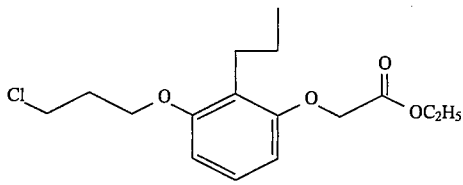

The compound of Example 37 (1.0 g, 4.20 mmol), 1-bromo-3-chloropropane (793 mg, 5.04 mmol), and potassium carbonate (870 mg, 6.30 mmol) were added to 20 ml of methyl ethyl ketone and the reaction mixture was refluxed overnight. The solvent was removed under vacuum and 10 ml of water was added to the residue. The solution was extracted 3 times with ethyl acetate. The combined ethyl acetate extracts were dried over magnesium sulfate, filtered, and the solvent was removed under vacuum to give an oil as the crude product. Chromatography of the crude product on silica gel using 10/90 ethyl acetate/hexane as eluant gave the product as a colorless oil (1.2 g).

Analysis calculated for: $C_{16}H_{23}ClO_4$ (314.81) Calculated: C, 61.04; H, 7.36; Cl, 11.26 Found: C, 61.24; H, 7.50; Cl, 11.55

EXAMPLE 39

Ethyl [3-(3-iodopropoxy)-2-propylphenoxy]acetate

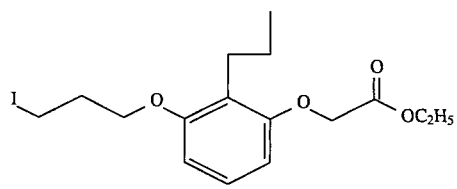

The compound of Example 38 (1.13 g) and sodium iodide (4.39 g) were added to 100 ml of methyl ethyl ketone and the reaction mixture was heated to reflux overnight. The solvent was removed under vacuum and water was added to the residue. The solution was extracted with ethyl acetate (3 times) and the combined extracts were dried over magnesium sulfate and filtered. The solvent was removed under vacuum to give the product as an oil (1.5 g).

EXAMPLE 40

2,4-Dihydroxy-3-propylbenzamide

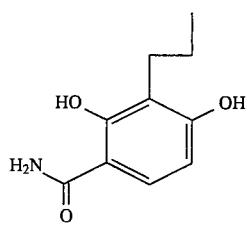

2,4-Dihydroxy-3-(2-propenyl)benzamide (575 mg) and 125 ml of ethanol was hydrogenated at 5 psi, room temperature, using 4% Pd/C catalyst for 3 hours. The solvent was removed under vacuum to give the product as an oil (4.25 mg, 74%).

EXAMPLE 41

Ethyl [3-[3-[4-(aminocarbonyl)-3-hydroxy-2-propylphenoxy]propoxy]-2-propylphenoxy]acetate

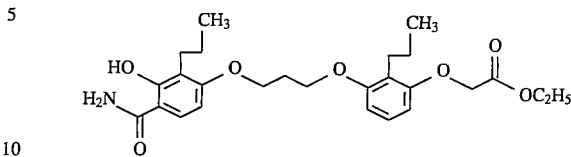

The compound of Example 40 (195 mg, 1.0 mmol), the compound of Example 39 (406 mg, 1.0 mmol) and potassium carbonate (276 mg, 2.0 mmol) were added to 2.0 ml of DMF. The reaction mixture was stirred at room temperature overnight then 15 ml of water was added to the reaction mixture, and it was extracted three times with ethyl acetate. The combined organic layers were washed once with water, dried over magnesium sulfate, and filtered. The solvent was removed under vacuum to give an oil. Chromatography of the oil on silica gel with 60/40 ethyl acetate/hexane as eluant gave the product.

EXAMPLE 42

Ethyl [3-[3-[4-(aminocarbonyl)-3-methoxy-2-propylphenoxy]propoxy]-2-propylphenoxy]acetate

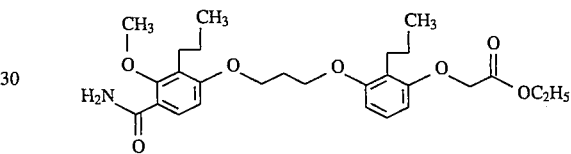

The compound of Example 41 (134 mg), potassium hydroxide (18 mg) and dimethyl sulfate (53 mg) were added to 2.0 ml of THF and the reaction mixture was stirred at room temperature overnight. Water (10 ml) was added, and the reaction mixture was extracted three times with ethyl acetate. The combined organic extracts were dried over anhydrous magnesium sulfate, filtered, and the solvent was removed under vacuum to give an oil. Chromatography of the oil on silica gel with 50/50 ethyl acetate/hexane as eluant gave the product as a colorless gum.

EXAMPLE 43

[3-[3-[4-(Aminocarbonyl)-3-methoxy-2-propylphenoxy]propoxy]-2-propylphenoxy]acetic acid

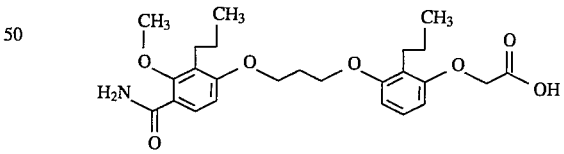

The compound of Example 42 (90 mg, 0.1845 mmol) and 369 µl of 1M lithium hydroxide were added to 2.0 ml of methanol, and the reaction mixture was stirred at room temperature overnight. The solvent was removed under vacuum, 10 ml of water was added, and the solution was acidified with dilute hydrochloric acid then stirred for 1 hour. The white precipitate that formed was removed by filtration and dried at 40° C. in a vacuum oven to give the product.

Analysis calculated for: $C_{25}H_{33}NO_7$ (459.54) Calculated: C, 65.34; H, 7.24; N, 3.05 Found: C, 65.26; H, 7.30; N, 2.94

EXAMPLE 44

Ethyl [3-[3-[3-hydroxy-4-[(methylamino) carbonyl]-2-propylphenoxy]propoxy]-2-propylphenoxy]acetate

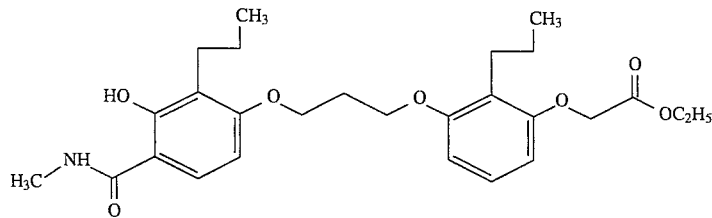

2,4-Dihydroxy-N-methyl-3-propylbenzamide (209 mg, 1 mmol), the compound of Example 39 (406 mg, 1 mmol) and potassium carbonate (276 mg, 2 mmol) were added to 2.0 ml of DMF. The reaction mixture was stirred at room temperature overnight and then partitioned between ethyl acetate and water. The organic layer was separated, washed once with water and dried over magnesium sulfate. Solvents were removed under vacuum to give a crude oil which was purified by chromatography on silica gel using 60/40 ethyl acetate/hexane as eluant to give the product (100 mg).

EXAMPLE 45

Ethyl [3-[3-[3-methoxy-4-[(methylamino) carbonyl]-2-propylphenoxy]propoxy]-2-propylphenoxy]acetate

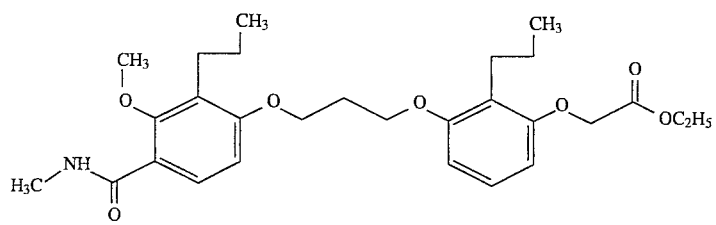

The compound of Example 44 (105 mg, 0.2153 mmol), dimethyl sulfate (40.7 mg, 0.3229 mmol) and potassium hydroxide (15 mg, 0.2583 mmol) were added to 2.0 ml of THF. The reaction mixture was stirred at room temperature overnight, and then 10 ml of water was added. The mixture was extracted three times with ethyl acetate, and the extracts were combined and dried over anhydrous magnesium sulfate then filtered, and the solvent was removed under vacuum to give an oil. Chromatography of the oil on silica gel with 50/50 ethyl acetate/hexane as eluant gave the product as a colorless gum.

EXAMPLE 46

[3-[3-[3-Methoxy-4-[(methylamino)carbonyl]-2-propylphenoxy]propoxy]-2-propylphenoxy]acetic acid

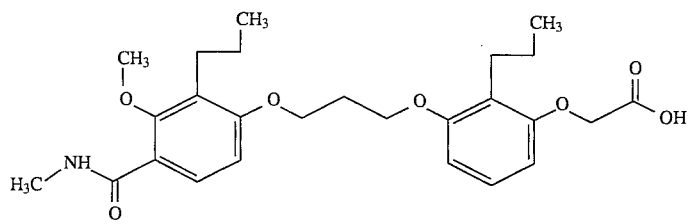

The compound of Example 45 (70 mg, 0.1395 mmol) and 279 µl of 1M lithium hydroxide was added to 2.0 ml of methanol, and the reaction mixture was stirred at room temperature overnight. The solvent was removed under vacuum and 2.0 ml of water was added, and the solution was acidified with 10% hydrochloric acid and then extracted three times with ethyl acetate. The extracts were combined and the solvent was removed under vacuum to give the product.

Analysis calculated for: $C_{26}H_{35}NO_7$ (478.05) Calculated: C, 65.32; H, 7.49; N, 2.93 Found : C, 65.03; H, 7.57; N, 2.76

DMF. The reaction mixture was stirred at room temperature overnight and then 15.0 ml of water was added to the reaction mixture, and it was extracted three times with ethyl acetate. The combined organic layers were washed once with water, dried over magnesium sulfate and filtered. The solvent was removed under vacuum to give an oil which was purified by chromatography on silica gel with 60/40 ethyl acetate/hexane as eluant to give the title compound (160 mg).

EXAMPLE 49

Ethyl [3-[3-[3-methoxy-2-propyl-4-(1-pyrrolidinylcarbonyl)phenoxy]propoxy]-2-propylphenoxy]acetate

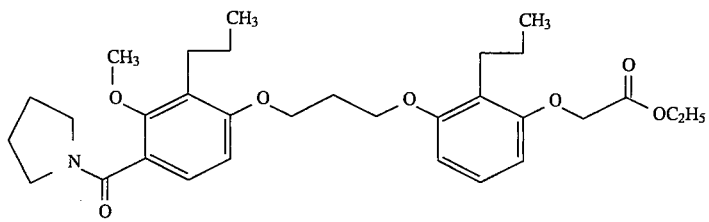

EXAMPLE 47

1-(2,4-Dihydroxy-3-propylbenzoyl)pyrrolidine

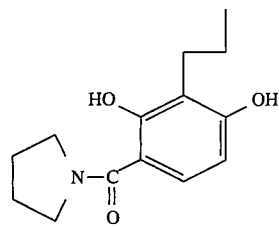

1-[2,4-dihydroxy-3-(2-propenyl)benzoyl]pyrrolidine (750 mg) in 2 ml ethanol was hydrogenated at room temperature and 5 psi for three hours using 4% Pd/C as catalyst. The solvent was removed under vacuum and the residue was chromatographed on silica gel using 50/50 ethyl acetate/hexane as eluant to give the product (650 mg).

EXAMPLE 48

Ethyl [3-[3-[3-hydroxy-2-propyl-4-(1-pyrrolidinylcarbonyl)phenoxy]propoxy]-2-propylphenoxy]acetate The compound of Example 48 (200 mg, 0.3789 mmol) was added to 2.0 ml of THF then potassium hydroxide (25.5 mg, 0.4546 mmol) was added followed by dimethyl sulfate (71.7 mg, 0.5683 mmol), and the reaction mixture was stirred at room temperature overnight. The reaction mixture was poured into water and extracted three times with ethyl acetate and the combined extracts were dried over anhydrous magnesium sulfate and filtered. The solvent was removed under vacuum to give an oil. Chromatography of the oil on silica gel with 50/50 ethyl acetate/hexane as eluant gave the product.

EXAMPLE 50

Ethyl [3-[3-methoxy-2-propyl-4-(1-pyrrolidinylcarbonyl)phenoxy]propoxy]-2-propylphenoxy]acetic acid

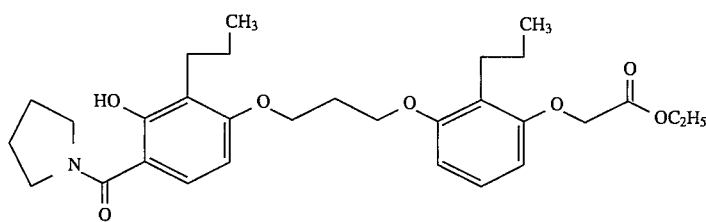

The compound of Example 47 (249 mg, 1.0 mmol), the compound of Example 39 (406 mg, 1.0 mmol) and potassium carbonate (276 mg, 2.0 mmol) were added to 2.0 ml of

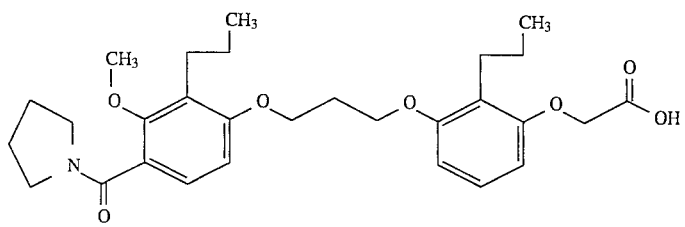

The compound of Example 49 (150 mg, 0.2769 mmol) and 1M lithium hydroxide (554 μl, 0. 5538 mmol) were added to 2.0 ml of methanol and the reaction mixture was stirred at room temperature overnight. The solvent was removed under vacuum, 2.0 ml of water was added, then the solution was acidified with 10% hydrochloric acid. The solution was extracted three times with ethyl acetate and the combined extracts were dried and filtered. The solvent was removed under vacuum to give the product as a gum.

Analysis calculated for: $C_{29}H_{39}NO_7 \cdot 0.5H_2O$ (522.648) Calculated: C, 66.65; H, 7.71; N, 2.68 Found: C, 66.52; H, 7.86; N, 2.55

EXAMPLE 51

Ethyl [3-[3-[3-hydroxy-4-[(methylamino) carbonyl]-2-(2-propenyl)phenoxy]propoxy]-2-propylphenoxy]acetate

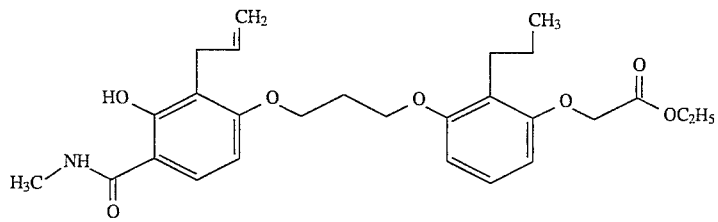

Ethyl [3-(3-chloropropxy)-2-propylphenoxy]acetate (386 mg), 2,4-dihydroxy-N-methyl-3-(2-propenyl)benzamide (207 mg), potassium carbonate (276 mg) and sodium iodide (299 mg) were added to 2.0 ml of DMF, and the reaction mixture was heated over a 60° C. oil bath overnight. The reaction mixture was poured into 10 ml of water and extracted three times with ethyl acetate. The combined ethyl acetate extracts were washed twice with water, dried, and filtered. The solvent was removed under vacuum to give an oil. The oil was then chromatographed on silica gel with 50/50 ethyl acetate/hexane as eluant to give the product (100 mg).

EXAMPLE 52

Ethyl [3-[3-[3-methoxy-4-[(methylamino) carbonyl]-2-(2-propenyl)phenoxy]propoxy]-2-propylphenoxy]acetate

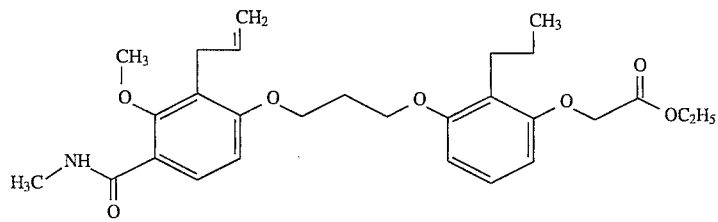

The compound of Example 51 (120 mg, 0.247 mmol), potassium hydroxide (16.6 mg, 0.285 mmol) and dimethyl sulfate (46.7 mg, 0.37 mmol) were added to 5.0 ml of THF, and the reaction mixture was stirred at room temperature overnight. The solvent was removed under vacuum, and 10 ml of water was added. The solution was extracted three times with ethyl acetate, the combined extracts were dried, and the solvent was removed under vacuum to give an oil. Chromatography of the oil on silica gel using 50/50 ethyl acetate/hexane as eluant gave the product as a colorless gum.

EXAMPLE 53

[3-[3-[3-Methoxy-4-[(methylamino)carbonyl]-2-(2-propenyl)phenoxy]propoxy]-2-propylphenoxy]acetic acid

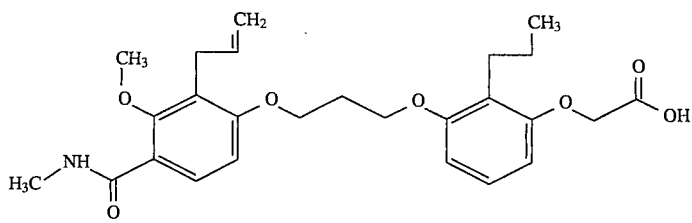

The compound of Example 52 (95 mg, 0.19 mmol) and 380 µl (0.38 mmol) of 1M lithium hydroxide were added to 2.0 ml of methanol, and the reaction mixture was stirred for four hours at room temperature. The solvent was removed under vacuum to give a white solid which was suspended in 5.0 ml of water. The mixture was acidified with 10% hydrochloric acid, stirred and filtered to remove the resultant solid which was then dried at 40° C. overnight in a vacuum oven to give the product.

Analysis calculated for: $C_{26}H_{33}NO_7$(471.556) Calculated: C, 66.23; H, 7.05; N, 2.97 Found: C, 66.09; H, 7.09; N, 2.90

EXAMPLE 54

Ethyl [3-[3-[4-(aminocarbonyl)-3-hydroxy-2-(2-propenyl)phenoxy]propoxy]-2-propylphenoxy]acetate

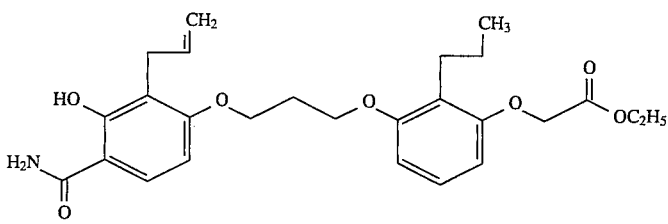

2,4-Dihydroxy-3-(2-propenyl)benzamide (193 mg 1.0 mmol), ethyl [3-(3-chloropropoxy)-2-propylphenoxy]acetate(386 mg, 1.0 mmol), sodium iodide (276 mg, 2.0 mmol), and potassium carbonate (276 mg, 2.0 mmol) were added to 2.0 ml of DMF, and the reaction mixture was heated in an oil bath at 40° C. overnight. The temperature was raised to 60° C., and the reaction mixture was again heated overnight. The reaction mixture was poured into 15 ml of water and extracted three times with ethyl acetate. The combined extracts were washed twice with water, dried and filtered. The solvent was removed under vacuum to give the crude product as a solid. Chromatography of the crude product on silica gel with 50/50 ethyl acetate/hexane as eluant gave the product.

EXAMPLE 55

Ethyl [3-[3-[4-(aminocarbonyl)-3-methoxy-2-(2-propenyl)phenoxy]propoxy]-2-propylphenoxy]acetate

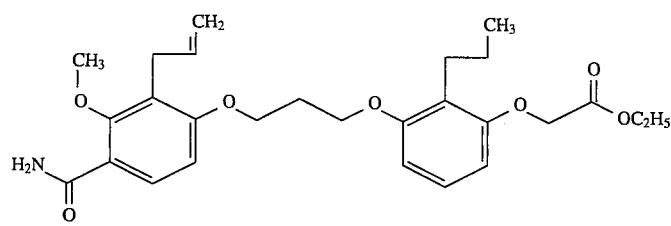

The compound of Example 54 (132 mg, 0.280 mmol), potassium hydroxide (18.8 mg, 0.336 mmol) and dimethyl sulfate (52.9 mg, 0.420 mmol) were added to THF, and the reaction mixture was stirred overnight at room temperature, then 10 ml of water was added, and the layers were separated. The aqueous layer was extracted three times with ethyl acetate, and the combined organic fractions were dried and filtered. The solvent was removed under vacuum to give an oil. Chromatography of the oil on silica gel with 50/50 ethyl acetate/hexane gave the product as a white solid.

EXAMPLE 56

[3-[3-[4-(Aminocarbonyl)-3-methoxy-2-(2-propenyl)phenoxy]propoxy]-2-propylphenoxy]acetic acid

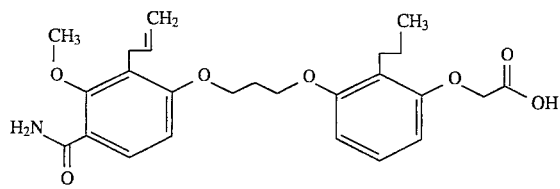

The compound of Example 55 (100 mg, 0.195 mmol) and 390 μl of 1M lithium hydroxide (0.3896 mmol) were added to 2.0 ml of methanol, and the reaction mixture was stirred at room temperature for 4 hours. The solvent was removed under vacuum, 5.0 ml of water was added to the residue, and the mixture was acidified with 10% hydrochloric acid. The mixture was filtered, and the white solid which was recovered was dried in a 40° C. oven overnight to give the product.

Analysis calculated for: $C_{25}H_{31}NO_7$ Calculated: C, 65.63; H, 6.83; N, 3.06 Found: C, 65.48; H, 6.81; N, 2.95

EXAMPLE 57

Ethyl [3-[3-[3-hydroxy-2-(2-propenyl)-4-(1-pyrrolidinylcarbonyl)phenoxy]propoxy]- 2-propylphenoxy]acetate

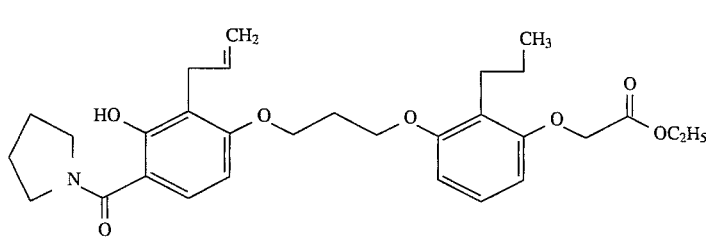

1-[2,4-Dihydroxy-3-(2-propenyl)benzoyl]pyrrolidine (198.6 mg, 0.803 mmol), ethyl [3-(3-chloropropoxy)-2-propylphenoxy]acetate (310 mg, 0.803 mmol), sodium iodide (240 mg, 1.606 mmol) and potassium carbonate were added to 3.0 ml of DMF. The reaction mixture was heated at 60° C. for 24 hours then poured into 15 ml of water and extracted three times with ethyl acetate. The combined extracts were washed twice with water, dried and filtered. The solvent was removed under vacuum to give the crude product. Chromatography of the crude product on silica gel with 50/50 ethyl acetate/hexane gave the product (145 mg).

EXAMPLE 58

Ethyl [3-[3-[3-methoxy-2-(2-propenyl)-4-(1-pyrrolidinylcarbonyl)phenoxy]propoxy]- 2-propylphenoxy]acetate

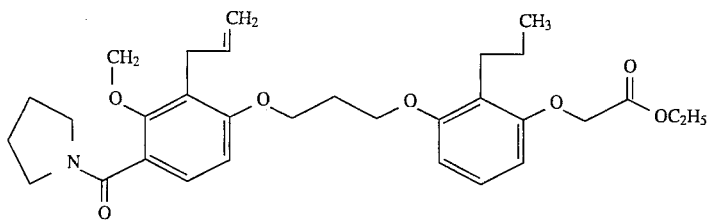

The compound of Example 57 (135 mg, 0.257 mmol), potassium hydroxide (17.29 mg, 0.308 mmol) and dimethyl sulfate (48.6 mg, 0.385 mmol) were added to 2.0 ml THF, and the reaction mixture was stirred overnight at room temperature. Water (10 ml) was added, and the mixture was extracted three times with ethyl acetate. The combined extracts were dried and filtered and the solvent was removed under vacuum to give an oil. Chromatography of the oil on silica gel with 50/50 hexane/ethyl acetate as eluant gave the product as a colorless oil.

EXAMPLE 59

[3-[3-[3-Methoxy-2-(2-propenyl)-4-(1-pyrrolidinylcarbonyl)phenoxy]propoxy]- 2-propylphenoxy]acetic acid

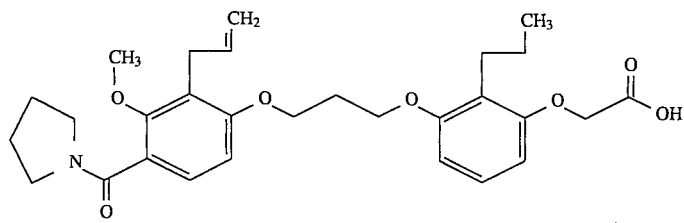

The compound of Example 58 (95 mg, 0.176 mmol) and 352 µl (0.352 mmol) of 1M lithium hydroxide were added to 2.0 ml of methanol. The reaction mixture was stirred at room temperature for 4 hours and the solvent was removed under vacuum. Water (5.0 ml) was added to the residue, and the mixture was acidified with 10% hydrochloric acid then extracted three times with ethyl acetate. The combined organic extracts were dried over anhydrous magnesium sulfate and filtered. The solvent was removed under vacuum to give a gum. Chromatography of the gum on silica gel with 50/50 ethyl acetate/hexane as eluant followed by drying under vacuum overnight gave the product.

Analysis calculated for: $C_{29}H_{37}NO_7 \cdot 0.125H_2O$ (513.86) Calculated: C, 67.78; H, 7.31; N, 2.73 Found: C, 67.53; H, 7.26; N, 2.60

EXAMPLE 60

Ethyl 7-[3-[2-(cyclopropylmethyl)-3-hydroxy-4-[(methylamino)carbonyl]phenoxy]propoxy]-3,4-dihydro-8-propyl-2H-1-benzopyran-2-propanoate ran-2-propanoate (685 mg, 1.53 mmol), and potassium carbonate (276 mg, 2.00 mmol) were added to 2.0 ml of DMF, and the reaction mixture was stirred at room temperature overnight. Water (50 ml) was added to the reaction mixture and it was extracted four times with 30 ml aliquots of ethyl acetate. The combined ethyl acetate extracts were washed with water, then dried over magnesium sulfate, filtered and concentrated in vacuo to give a brown oil. Chromatography of the oil on silica gel with 30/70 ethyl acetate/hexane as eluant gave the product as a white solid (200 mg).

EXAMPLE 61

Ethyl 7-[3-[2-(cyclopropylmethyl)-3-methoxy-4-[(methylamino)carbonyl]phenoxy]propoxy]-3,4-dihydro-8-propyl-2H-1-benzopyran-2-propanoate

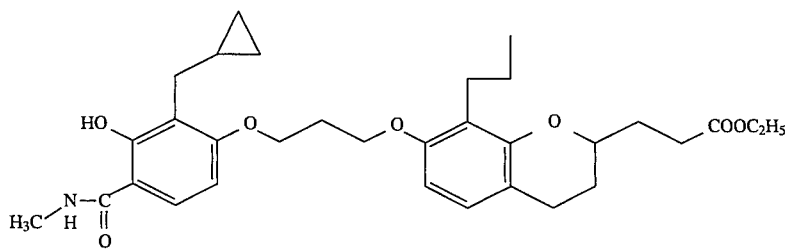

The compound of Example 16 (340 mg, 1.53 mmol), ethyl 3,4-dihydro- 7-(3-iodopropoxy)-8-propyl-2H-1-benzopy-

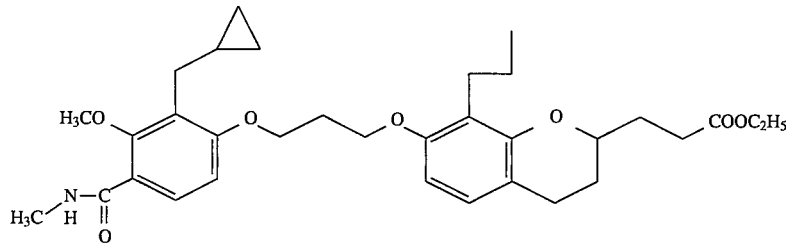

The compound of Example 60 (170 mg, 0.31 mmol) was added to about 5.0 ml of THF. Potassium hydroxide (21.2 mg, 0.38 mmol) was added and the mixture was stirred for 10 min. Dimethyl sulfate (59.6 mg, 0.47 mmol) was added, and the reaction mixture was stirred for 4 hours at room temperature. Water (10 ml) was added to the reaction mixture, and it was extracted three times with ethyl acetate. The combined extracts were filtered, and the solvent was removed under vacuum to give an oil. Chromatography of the oil on silica gel with 40/60 ethyl acetate/hexane gave the product as a colorless oil (160 mg).

EXAMPLE 62

7-[3-[2-(Cyclopropylmethyl)-3-methoxy-4-[(methylamino)carbonyl]phenoxy]propoxy]-3,4-dihydro-8-propyl-2H-1-benzopyran-2-propanoic acid

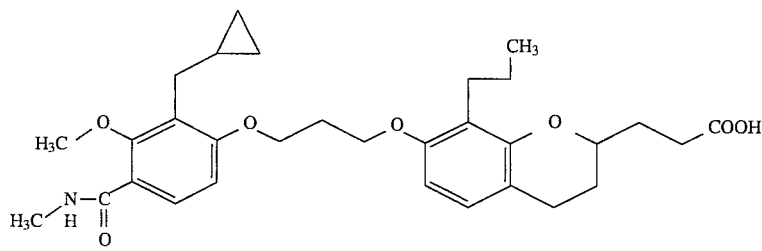

The compound of Example 60 (140 mg, 0.2465 mmol) was added to 493 μl of 1M lithium hydroxide and 2.0 ml of methanol, and the reaction mixture was stirred at room temperature overnight. The solvent was removed under vacuum, 6.0 ml of water was added to the residue, and it was acidified with 10% hydrochloric acid. The mixture was extracted three times with 10 ml of ethyl acetate and the combined extracts were dried over anhydrous magnesium sulfate and filtered. The solvent was removed under vacuum to give a gum. Removal of additional solvent under high vacuum overnight gave the product as a white solid.

Analysis calculated for $C_{31}H_{41}NO_7 \cdot 1/2\ H_2O$ (548.68) Calculated: C, 67.81; H, 7.72; N, 2.55 Found: C, 67.86; H, 7.74; N, 2.45

The above (±) compound was separated into its constituent isomers. The (+) isomer and the (−)-isomer were separated by chiral column chromatography using Chiracel OD using 5% isopropanol:95% hexane:0.1% trifluoroacetic acid as the eluant. The (+) isomer had a optical rotation of $[\alpha]_{589}=57.3°\ [\pm 4°]$ and the (−) isomer had an optical rotation of $[\alpha]_{589}=-63.2°\ [\pm 4°]$.

EXAMPLE 63

Ethyl [3-[3-[2-(cyclopropylmethyl)-3-hydroxy-4-[(methylamino)carbonyl]phenoxy]propoxy]-2-propylphenoxy]acetate The compound of Example 39 and the compound of Example 16 are reacted together under the conditions described in Example 44. The crude product thus obtained, is purified by chromatography on silica gel using ethyl acetate/hexane (3:7) as eluant.

EXAMPLE 64

Ethyl [3-[3-[2-(cyclopropylmethyl)-3-methoxy-4-[(methylamino)carbonyl]phenoxy]propoxy]-2-acetate

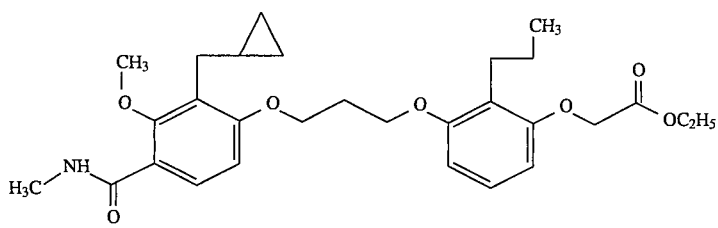

The compound of Example 63 is methylated (Me₂SO₄, KOH, THF) under the conditions described in Example 45. Chromatographic purification of the crude product on silica gel (Ethyl acetate/hexane (3:7) as eluant) affords the product.

EXAMPLE 65

[3-[2-(Cyclopropylmethyl)-3-methoxy-4-(methylamino)carbonyl]phenoxy]propoxy]-2-propylphenoxy]acetic acid

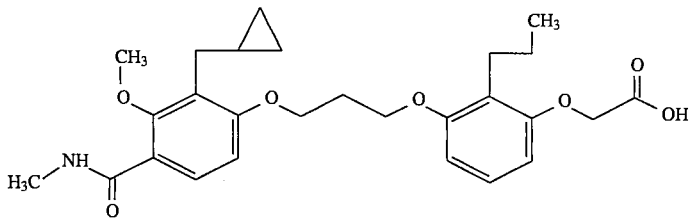

The compound of Example 64 is saponified under the conditions described in Example 46. Chromatographic purification of the crude acid on silica gel affords the title compound.

EXAMPLE 66

3-(Cyclopropylmethyl)-2,4-dihydroxy benzamide

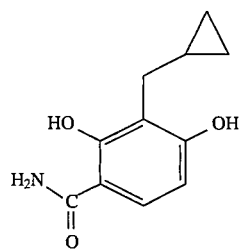

The compound of Example 15 is heated at 50° C. in a saturated ammonium chloride solution overnight. The reaction mixture is thoroughly extracted with ethyl acetate, and the solvent dried (Na₂SO₄) and evaporated in vacuo to afford the crude product. Chromatographic purification or silica gel using ethyl acetate/hexane (4:6) as eluant affords the product.

EXAMPLE 67

Methyl 7-[3-[4-(aminocarbonyl)-2-(cyclopropylmethyl)-3-hydroxyphenoxy]propoxy]-8-propyl-2H-1-benzopyran-2-carboxylate

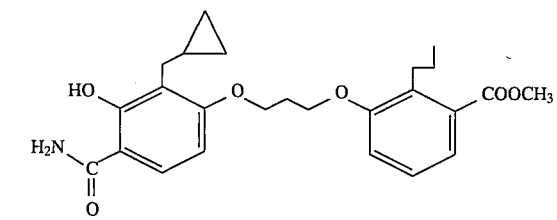

The compound of Example 66 and the compound of Example 23 are reacted together under the conditions described in Example 24. The crude product is purified by chromatography on silica gel using ethyl acetate/hexane (4:6) as eluant to afford the product.

EXAMPLE 68

Methyl 7-[3-[4-(aminocarbonyl)-2-(cyclopropylmethyl)-3-methoxyphenoxy]propoxy]-8-propyl-2H-1-benzopyran-2-carboxylate

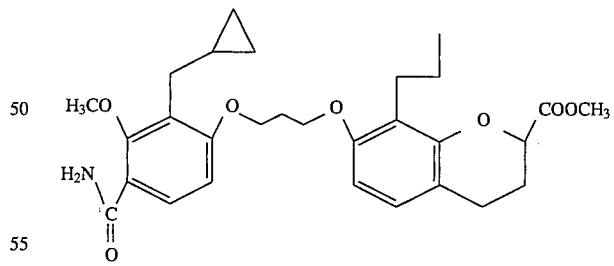

The compound of Example 67 is exposed to the conditions described in Example 25. Chromatography of the crude product on silica gel using ethyl acetate/hexane, (3:7) as eluant affords the product.

EXAMPLE 69

7-[3-[4-(Aminocarbonyl)-2-(cyclopropylmethyl)-3-methoxy phenoxy]propoxy]-3,4-dihydro-8-propyl-2H-1-benzopyran-2-carboxylic acid

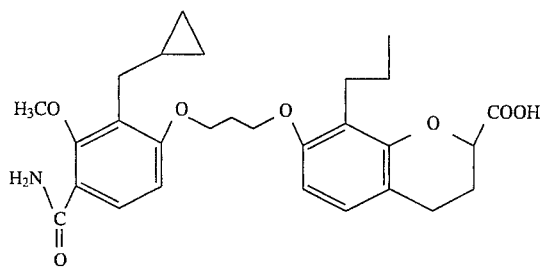

The compound of Example 68 is saponified with lithium hydroxide using the conditions described in Example 26. Chromatography of the crude residue on silica gel using ethyl acetate/methanol/acetic acid as eluant (90:9.5:0.5) gives the product.

EXAMPLE 70

Ethyl [3-[3-[4-(aminocarbonyl)-2-(cyclopropylmethyl)-3-hydroxyphenoxy]propoxy]-2-propylphenoxy]acetate

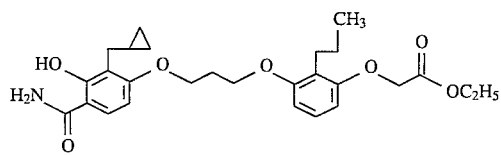

The compound of Example 66 and the compound of Example 39 are reacted together under the conditions described in Example 24. The crude product is purified by chromatography on silica gel using ethyl acetate/hexane 4:6 as eluant to afford the title compound.

EXAMPLE 71

Ethyl [3-[3-[4-(aminocarbonyl)-2-(cyclopropylmethyl)-3-methoxyphenoxy]propoxy]-2-propylphenoxy]acetate

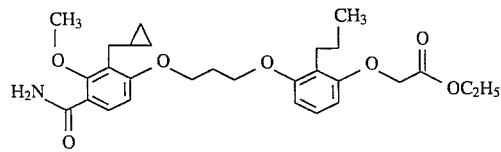

The compound of Example 70 is exposed to the conditions described in Example 25. Chromatography of the crude product on silica gel using ethyl acetate/hexane, (3:7) as eluant affords the product.

EXAMPLE 72

[3-[3-[4-(Aminocarbonyl)-2-(cyclopropylmethyl)-3-methoxyphenoxy]propoxy]-2-propylphenoxy]acetic acid

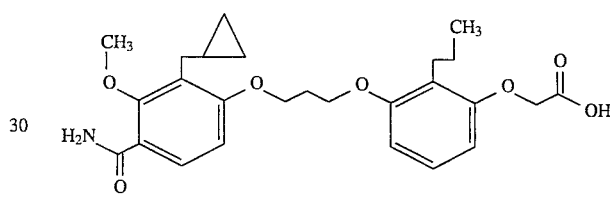

The compound of Example 71 is saponified with lithium hydroxide using the conditions described in Example 26. Chromatography of the crude residue on silica gel using ethyl acetate/methanol/acetic acid as eluant (90:9.5:0.5) affords the product.

EXAMPLE 73

Methyl 7-[3-[4-(aminocarbonyl)-2-(cyclopropylmethyl)-3-hydroxyphenoxy]propoxy]-3,4-dihydro-8-propyl-2H-1-benzopyran- 2-propanoate

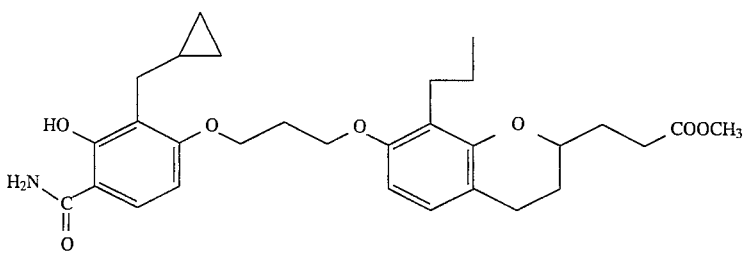

The compound of Example 66 and the compound of Example 3 are coupled under the conditions outlined in Example 60. Chromatography of the crude phenolic ester on silica gel using ethyl acetate/hexane (3:7) as eluant affords the product.

EXAMPLE 74

Methyl 7-[3-[4-(aminocarbonyl)-2-(cyclopropylmethyl)-3-methoxyphenoxy]propoxy]-3,4-dihydro-8-propyl-2H-1-benzopyran- 2-propanoate

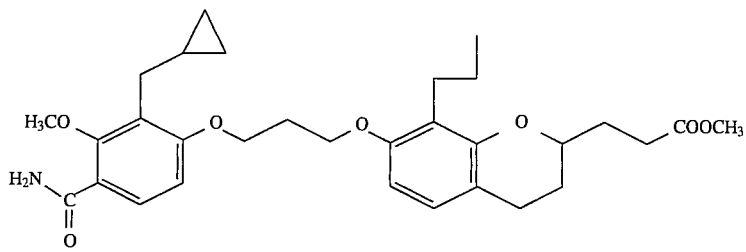

The compound of Example 73 is treated with dimethyl sulfate and KOH in THF under the conditions described in Example 61. Chromatographic purification of the crude product on silica gel using ethyl acetate/hexane (4:6) as eluant affords the product.

EXAMPLE 75

7-[3-[4-(Aminocarbonyl)-2-(cyclopropylmethyl)-3-methoxyphenoxy]propoxy]-3,4-dihydro-8-propyl-2H-1-benzopyran- 2-propanoic acid

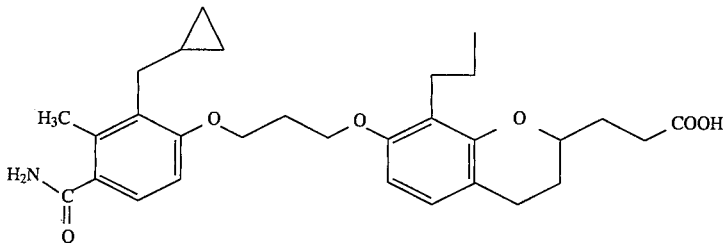

The compound of Example 74 is saponified as described in Example 62. Chromatography on silica gel with ethyl acetate/methanol/acetic acid (95:4.5:0.5) as eluant gives the product.

EXAMPLE 76

Methyl 7-[3-[4-(aminocarbonyl)-3-hydroxy-2-(2-propenyl)phenoxy]propoxy]-3,4-dihydro-8-propyl-2H-1-benzopyran- 2-propanoate

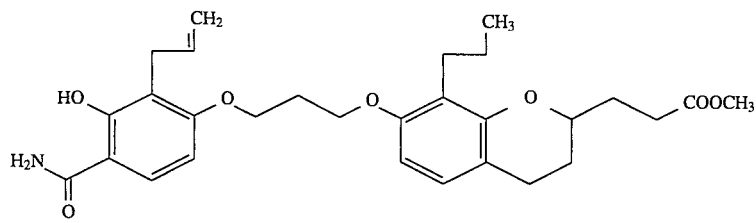

The compound of Example 20 and the compound of Example 3 are coupled as described in Example 60. Chromatographic purification of the crude phenolic ester on silica gel using ethyl acetate/hexane (3:7) as eluant affords the product.

EXAMPLE 77

Methyl 7-[3-[4-(aminocarbonyl)-3-methoxy-2-(2-propenyl)phenoxy]propoxy]-3,427-dihydro-8-propyl-2H-1-benzopyran- 2-propanoate

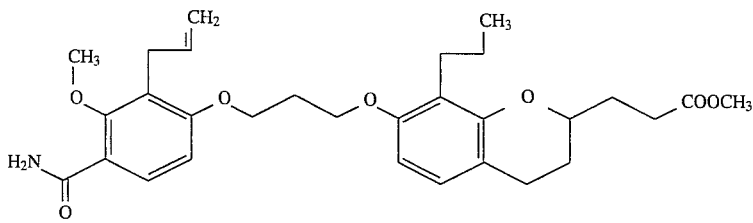

The compound of Example 76 is methylated using the conditions described in Example 61. After ethyl acetate extraction of the reaction mixture as in Example 61, the crude product is purified by chromatography on silica gel using ethyl acetate/hexane (4:6) as eluant, to provide the product.

EXAMPLE 78

7-[3-[4-(Aminocarbonyl)-3-methoxy-2-(2-propenyl)phenoxy]propoxy]-3,4-dihydro-8-propyl-2H-1-benzopyran-2-propanoic acid

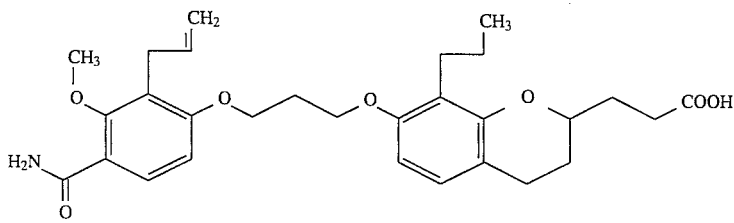

The ester of Example 77 is saponified under the conditions described in Example 62. The product is obtained after silica gel chromatography of the crude residue using ethyl acetate/methanol/acetic acid (95:4.5:0.5) as eluant.

EXAMPLE 79

7-[3-[4-(Aminocarbonyl)-3-methoxy-2-propylphenoxy]propoxy]-3,4-dihydro-8-propyl-2H-1-benzopyran-2-propanoic acid

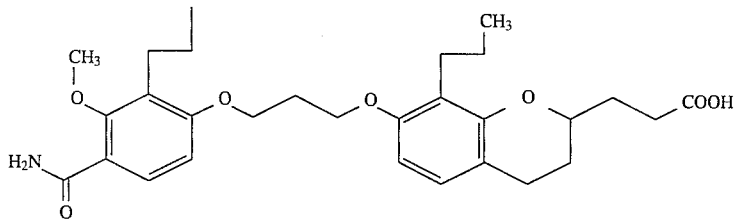

The compound of Example 78 is dissolved in ethanol and hydrogenated at room temperature and/atmospheric pressure with 5% Palladium on carbon as catalyst. The catalyst is removed by filtration through celite and the product is isolated by chromatography on silica gel using ethyl acetate/methanol/acetic acid (95:4.5:0.5) as eluant.

What is claimed is:

1. A compound of the formula:

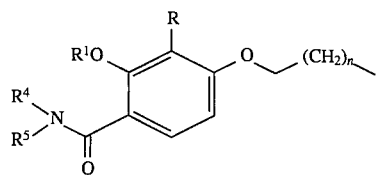

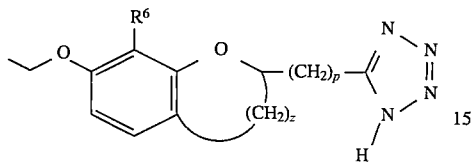

wherein

R represents alkyl having 1 to 6 carbon atoms, alkenyl having 2 to 6 carbon atoms, alkynyl having 2 to 6 carbon atoms, or —$(CH_2)_m$-$R^3$ wherein $R^3$ represents cycloalkyl of 3 to 5 carbons atoms and m is 1 or 2;

$R^1$ represents alkyl having 1 to 4 carbon atoms;

$R^6$ represents alkyl having 1 to 6 carbon atoms;

n is an integer from 1 to 5;

p is an integer from 0 to 6;

x is 0 or 2; and $R^4$ and $R^5$ are independently hydrogen or alkyl having 1 to 4 carbon atoms, or $R^4$ and $R^5$ together with N form a cycloalkylamine having 4 to 5 carbon atoms; and the stereoisomers and pharmaceutically acceptable salts thereof.

* * * * *